(12) United States Patent
Trieu

(10) Patent No.: US 7,879,027 B2
(45) Date of Patent: Feb. 1, 2011

(54) CONTROLLED RELEASE DEVICES FOR FUSION OF OSTEAL STRUCTURES

(75) Inventor: Hai H. Trieu, Cordova, TN (US)

(73) Assignee: Warsaw Orthopedic, Inc.

( * ) Notice: Subject to any disclaimer, the term of this patent is extended or adjusted under 35 U.S.C. 154(b) by 775 days.

(21) Appl. No.: 11/517,771

(22) Filed: Sep. 8, 2006

(65) Prior Publication Data

US 2007/0276337 A1 Nov. 29, 2007

Related U.S. Application Data

(63) Continuation-in-part of application No. 11/410,221, filed on Apr. 24, 2006.

(51) Int. Cl.
*A61K 9/22* (2006.01)
(52) U.S. Cl. .................. 604/892.1; 604/891.1; 604/65; 604/66; 623/17.12
(58) Field of Classification Search .............. 604/891.1, 604/892.1, 65, 66, 67; 623/17.11, 17.12, 623/17.13, 17.15, 17.16
See application file for complete search history.

(56) References Cited

U.S. PATENT DOCUMENTS

| | | | |
|---|---|---|---|
| 3,320,131 A | 5/1967 | Smith | |
| 3,941,127 A | 3/1976 | Froning | |
| 3,964,480 A | 6/1976 | Froning | |
| 4,039,682 A | 8/1977 | Ausman et al. | |
| 4,374,926 A | 2/1983 | Stern | |
| 4,430,760 A | 2/1984 | Smestad | |
| 4,439,423 A | 3/1984 | Smith | |
| 4,696,816 A | 9/1987 | Brown | |
| 4,719,108 A | 1/1988 | Smith | |
| 4,904,260 A | 2/1990 | Ray et al. | |
| 5,422,103 A | 6/1995 | Stern et al. | |
| 5,456,679 A * | 10/1995 | Balaban et al. | .......... 604/892.1 |
| 5,468,480 A | 11/1995 | Barrett et al. | |
| 5,645,549 A | 7/1997 | Boyd et al. | |
| 5,919,235 A | 7/1999 | Husson et al. | |
| 6,007,810 A | 12/1999 | Ishikawa et al. | |
| 6,063,378 A | 5/2000 | Nohara et al. | |
| 6,231,615 B1 | 5/2001 | Preissman | |
| 6,280,475 B1 | 8/2001 | Bao et al. | |
| 6,294,187 B1 | 9/2001 | Boyce et al. | |
| 6,471,688 B1 | 10/2002 | Harper et al. | |
| 6,491,666 B1 | 12/2002 | Santini, Jr. et al. | |
| 6,527,762 B1 | 3/2003 | Santini, Jr. et al. | |

(Continued)

FOREIGN PATENT DOCUMENTS

WO 9634093 10/1996

(Continued)

OTHER PUBLICATIONS

NCBI; "Fibroblast Growth Factor [Homo Sapiens]"; CAA41788; http:www.nebi.nlm.nih.gov/protein/1335059; printed on May 14, 2009; 2 pages.

(Continued)

*Primary Examiner*—Kevin C Sirmons
*Assistant Examiner*—Bhisma Mehta

(57) ABSTRACT

A device includes a first reservoir configured to include a degradation agent, a first control element configured to provide access to the first reservoir, and an expandable component configured to extend to engage an osteal structure.

9 Claims, 17 Drawing Sheets

U.S. PATENT DOCUMENTS

| | | | |
|---|---|---|---|
| 6,537,256 | B2 | 3/2003 | Santini, Jr. et al. |
| 6,551,838 | B2 | 4/2003 | Santini, Jr. et al. |
| 6,656,162 | B2 | 12/2003 | Santini, Jr. et al. |
| 6,669,683 | B2 | 12/2003 | Santini, Jr. et al. |
| 6,773,429 | B2 | 8/2004 | Sheppard, Jr. et al. |
| 6,827,250 | B2 | 12/2004 | Uhland et al. |
| 6,849,463 | B2 | 2/2005 | Santini, Jr. et al. |
| 6,973,718 | B2 | 12/2005 | Sheppard, Jr. et al. |
| 6,976,982 | B2 | 12/2005 | Santini, Jr. et al. |
| 7,014,636 | B2 | 3/2006 | Gilbert |
| 7,163,545 | B2 | 1/2007 | Yaszemski et al. |
| 7,169,405 | B2 | 1/2007 | Trieu |
| 7,217,293 | B2 | 5/2007 | Branch, Jr. |
| 2001/0020188 | A1 | 9/2001 | Sander |
| 2002/0026244 | A1 | 2/2002 | Trieu |
| 2002/0029083 | A1 | 3/2002 | Zucherman et al. |
| 2002/0087113 | A1 | 7/2002 | Hartlaub |
| 2002/0128202 | A1 | 9/2002 | Carney et al. |
| 2002/0173851 | A1 | 11/2002 | McKay |
| 2003/0009235 | A1 | 1/2003 | Manrique et al. |
| 2003/0039676 | A1 | 2/2003 | Boyce et al. |
| 2004/0031666 | A1 | 2/2004 | Ostman |
| 2004/0091540 | A1 | 5/2004 | Desrosiers et al. |
| 2004/0121486 | A1 | 6/2004 | Uhland et al. |
| 2004/0133280 | A1 | 7/2004 | Trieu |
| 2004/0143242 | A1* | 7/2004 | Ludin et al. ............ 604/891.1 |
| 2004/0220552 | A1 | 11/2004 | Heruth et al. |
| 2005/0031666 | A1 | 2/2005 | Trieu |
| 2005/0070778 | A1 | 3/2005 | Lackey et al. |
| 2005/0071009 | A1 | 3/2005 | Muhanna et al. |
| 2006/0004456 | A1 | 1/2006 | McKay |
| 2006/0046961 | A1 | 3/2006 | McKay et al. |
| 2006/0047341 | A1 | 3/2006 | Trieu |
| 2007/0003598 | A1 | 1/2007 | Trieu |
| 2007/0250044 | A1 | 10/2007 | Trieu |
| 2007/0250045 | A1 | 10/2007 | Trieu |
| 2007/0250046 | A1 | 10/2007 | Trieu |

FOREIGN PATENT DOCUMENTS

| | | | |
|---|---|---|---|
| WO | 0145577 | A2 | 6/2001 |
| WO | 01045577 | A3 | 6/2001 |
| WO | 0217824 | A2 | 3/2002 |
| WO | 02017824 | A3 | 3/2002 |
| WO | 03068149 | A2 | 8/2003 |
| WO | 2003068149 | A3 | 8/2003 |
| WO | 2004047691 | A | 6/2004 |
| WO | 2004101015 | A2 | 11/2004 |
| WO | 2005065079 | A2 | 7/2005 |
| WO | 20050065079 | A2 | 7/2005 |
| WO | 2005092249 | A1 | 10/2005 |
| WO | 2005102440 | A2 | 11/2005 |
| WO | 2005115438 | A1 | 12/2005 |
| WO | 2006017456 | A2 | 2/2006 |
| WO | 2006050106 | A | 5/2006 |
| WO | 2006055547 | A | 5/2006 |
| WO | 2007127548 | A | 11/2007 |

OTHER PUBLICATIONS

NCBI; "Albumin [Homo Sapiens]": CAA00606; http:www.nebi.nlm.nih.gov/protein/412163; printed on May 14, 2009; 2 pages.

NCBI; "Chymopapain [Carica Papaya]"; CAA66378; http:www.nebi.nlm.nih.gov/protein/1332461; printed on May 14, 2009; 2 pages.

NCBI; "Collagenase [Rattus Norvegicus]", CAA07432; http:www.nebi.nlm.nih.gov/protein/3242321; printed on May 14, 2009; 3 pages.

NCBI; "Morphogenetic Protein [Bacillus Subtilis Subsp. Subtilis Str. 168]"; NP_391481 http:www.nebi.nlm.nih.gov/protein/16080660, printed on May 14, 2009; 3 pages.

Sheikh H et al. 2009. In vivo intervertebral disc regeneration using stem cell-derived chondroprogenitors. J Neurosurg Spine 10: 265-272.

Bron JL et al. 2009. Repair, regenerative and supportive therapies of the annulus fibrosus: achievements and challenges. Eur Spine J 18:301-313.

Chymopapain from GenBank Accession No. CAA66378, pp. 1-2. Accessed May 14, 2009.

Collagenase from GenBank Accession No. CAA07432, pp. 1-3. Accessed May 14, 2009.

Fibroblast growth factor from GenBank Accession No. CAA41788, pp. 1-2. Accessed May 14, 2009.

Morphogenetic protein from GenBank Accession No. NP_391488, pp. 1-3, Accessed May 14, 2009.

Albumin from GenBank Accession No. CAA00606, pp. 1-2. Accessed May 14, 2009.

* cited by examiner

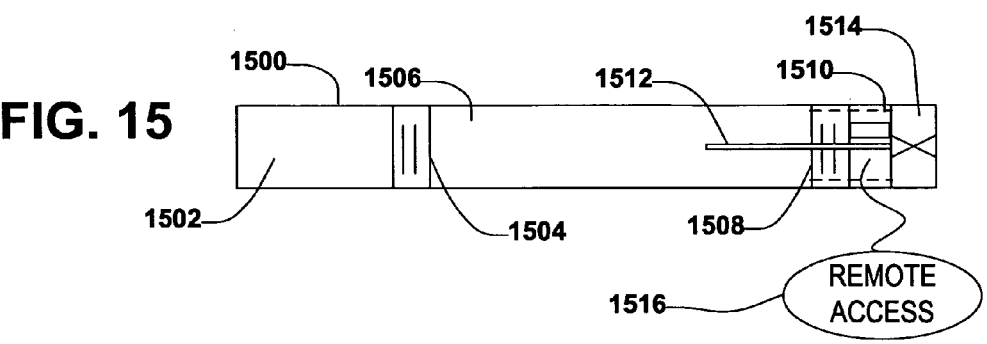
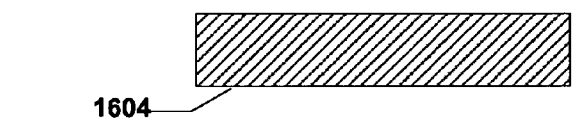
FIG. 16
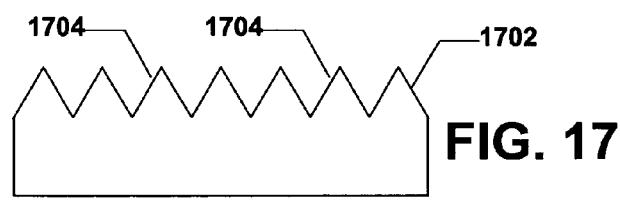
FIG. 17
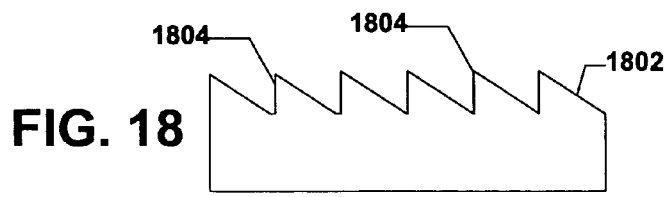
FIG. 18

CONTROLLED RELEASE DEVICES FOR FUSION OF OSTEAL STRUCTURES

CROSS-REFERENCE TO RELATED APPLICATION(S)

This application is a continuation-in-part and claims priority to U.S. application Ser. No. 11/410,221, entitled "CONTROLLED RELEASE DEVICES FOR THERAPEUTIC TREATMENTS OF SPINAL DISCS," filed Apr. 24, 2006 now U.S. Pat. No. 7,771,414, and naming inventor Hai H. Trieu, which is incorporated herein by reference in its entirety.

FIELD OF THE DISCLOSURE

The present disclosure relates generally to controlled release devices. More specifically, the present disclosure relates to controlled release devices for implanting in a soft tissue proximate to osteal structures.

BACKGROUND

In human anatomy, the spine is a generally flexible column that can withstand tensile and compressive loads. The spine also allows bending motion and provides a place of attachment for keels, muscles, and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Three joints reside between each set of two vertebrae: a larger intervertebral disc between the two vertebral bodies and two zygapophyseal joints located posterolaterally relative to the vertebral bodies and between opposing articular processes.

The intervertebral discs generally function as shock absorbers and as joints. Further, the intervertebral discs can absorb the compressive and tensile loads to which the spinal column can be subjected. At the same time, the intervertebral discs can allow adjacent vertebral bodies to move relative to each other, particularly during bending or flexure of the spine. Thus, the intervertebral discs are under constant muscular and gravitational pressure and generally, the intervertebral discs are the first parts of the lumbar spine to show signs of deterioration.

The zygapophyseal joints permit movement in the vertical direction, while limiting rotational motion of the two adjoining vertebrae. In addition, capsular ligaments surround the zygapophyseal joints, discouraging excess extension and torsion. In addition to intervertebral disc degradation, zygapophyseal joint degeneration is also common because the zygapophyseal joints are in almost constant motion with the spine. In fact, zygapophyseal joint degeneration and disc degeneration frequently occur together. Generally, although one can be the primary problem while the other is a secondary problem resulting from the altered mechanics of the spine, by the time surgical options are considered, both zygapophyseal joint degeneration and disc degeneration typically have occurred. For example, the altered mechanics of the zygapophyseal joints or the intervertebral disc can cause spinal stenosis, degenerative spondylolisthesis, and degenerative scoliosis.

Furthermore, acute strenuous events, such as whiplash or overextension, can damage capsular ligaments. Such damage to capsular ligaments if untreated can lead to degradation of the zygapophyseal joint or of the intervertebral disc.

In particular, deterioration can be manifested as a herniated disc. Weakness in an annulus fibrosis can result in a bulging of the nucleus pulposus or a herniation of the nucleus pulposus through the annulus fibrosis. Ultimately, weakness of the annulus fibrosis can result in a tear, permitting the nucleus pulposus to leak from the intervertebral space. Loss of the nucleus pulposus or a bulging of the nucleus pulposus can lead to pinching of nerves, causing pain and damage to vertebrae. In addition, aging can lead to a reduction in the hydration of the nucleus pulposus. Such a loss in hydration can also result in pinching of nerves.

A traditional option for treating a patient includes replacement of the intervertebral disc or the zygapophyseal joint with an implant. Another traditional option includes fusing adjacent vertebra using fasteners such as traditional screws or rods. However, such traditional methods are typically implemented with invasive surgical procedures. In particular, some traditional surgical procedures access the spine through the abdominal cavity, introducing risk to major organs and often leaving large scars.

BRIEF DESCRIPTION OF THE DRAWINGS

FIG. 9, FIG. 10, FIG. 11, FIG. 12, FIG. 13, FIG. 14, FIG. 15, and FIG. 16 include illustrations of exemplary controlled release devices;

FIG. 17 and FIG. 18 include cross section illustrations of exemplary surface features of an exemplary controlled release device;

DESCRIPTION OF DRAWINGS

Figure 1:
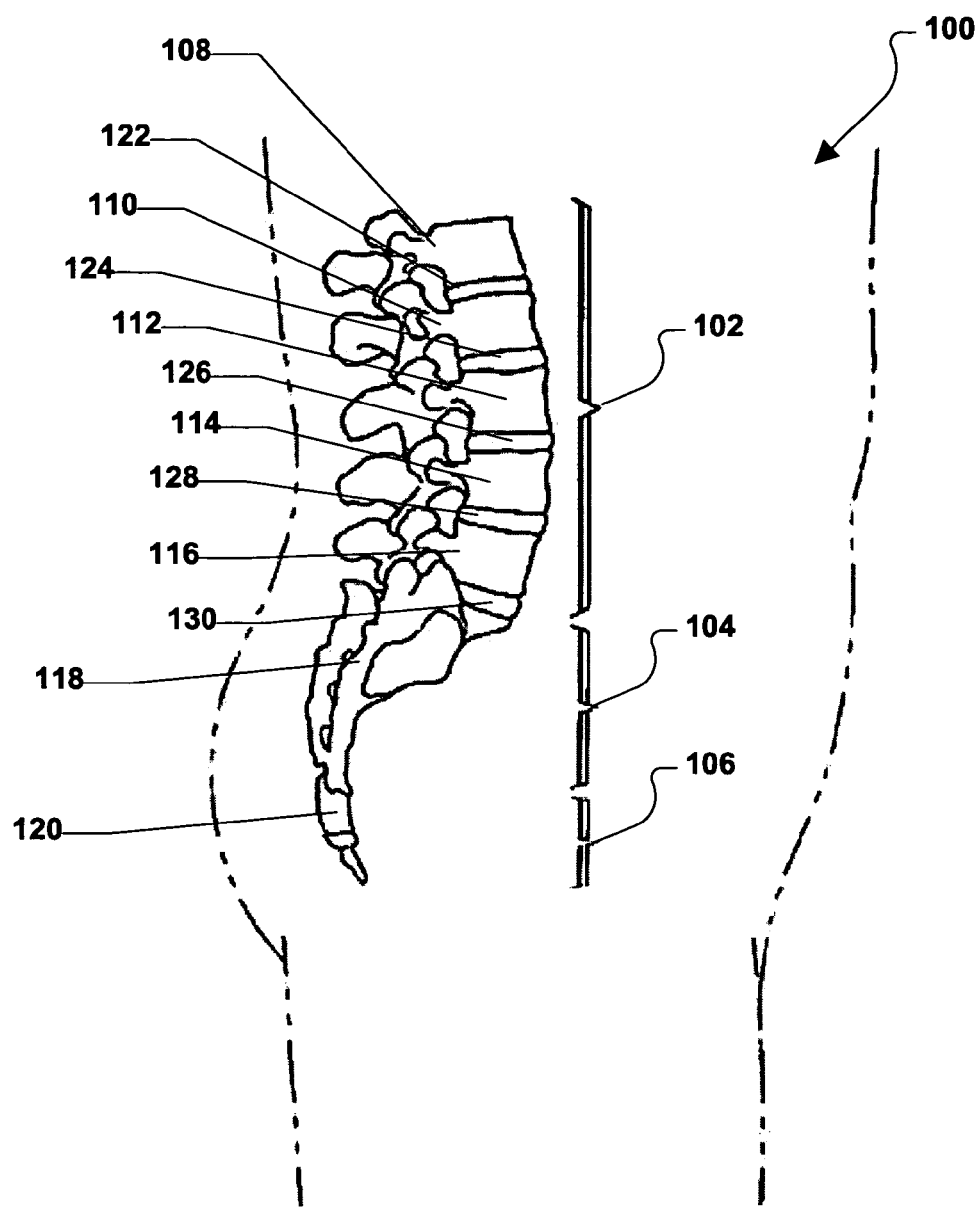
FIG. 1 includes a lateral view of a portion of a vertebral column.

In a particular embodiment, a controlled release device includes a control element connected to a reservoir. The control element provides access to the reservoir, which can result in release of agents configured to degrade soft tissue and encourage bone growth. In particular, the bone growth can result in the fusion of adjacent osteal structures, such as vertebral bodies and articular processes. In an example, the reservoir includes an agent, such as an osteogenerative agent or a degradation agent. In addition, the device can include a second reservoir. In addition, the controlled release device includes an expandable component configured to engage an osteal structure, such as a vertebra.

In an exemplary embodiment, a device includes a first reservoir configured to include a degradation agent, a first control element configured to provide access to the first reservoir, and an expandable component configured to extend to engage an osteal structure.

In another exemplary embodiment, a device includes a first reservoir configured to include a degradation agent, a second reservoir configured to include an osteogenerative agent, a first control element configured to provide access to the first reservoir, and a second control element configured to provide access to the second reservoir.

In a further exemplary embodiment, a device includes a first reservoir configured to include a degradation agent, a second reservoir configured to include an osteogenerative agent, a first valve in fluid communication with the first reservoir, and a second valve in fluid communication with the second reservoir. The first valve is configured to open in response to a first soft tissue condition, and the second valve is configured to open in response to a second soft tissue condition.

In an additional embodiment, a device includes a first reservoir configured to include an osteogenerative agent, a second reservoir configured to include a degradation agent, a first valve in fluid communication with the first reservoir, and a second valve in fluid communication with the second reservoir. The first valve is configured to open in response to a first soft tissue condition.

In another exemplary embodiment, a device includes a first reservoir configured to include an osteogenerative agent, a second reservoir configured to include a degradation agent, a first valve in fluid communication with the first reservoir, a second valve in fluid communication with the second reservoir, and an osmotic reservoir driver configured to apply pressure to at least one of the first or second reservoirs based on a condition of a tissue. The first valve is configured to open in response to a low-pressure condition in the first reservoir, and the second valve is configured to open in response to a high-pressure condition in the second reservoir.

In a further exemplary embodiment, a device includes a first reservoir configured to include an osteogenerative agent, a second reservoir configured to include a degradation agent, and a three-way valve configured to provide fluid communication with the first reservoir in response to a first tissue condition and configured to provide fluid communication with the second reservoir in response to a second tissue condition.

In an additional exemplary embodiment, a method of preparing a controlled release device includes selecting an osteogenerative agent, selecting a degradation agent, and selecting a valve configuration.

Description of Relevant Anatomy

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged or if one of the zygapophyseal joints is diseased, degenerated or damaged, that disc or joint can be at least partially treated with an implanted device according to one or more of the embodiments described herein. In a particular embodiment, a controlled release device can be inserted into the intervertebral lumbar disc 122, 124, 126, 128, 130 or a zygapophyseal joint.

Figure 2:
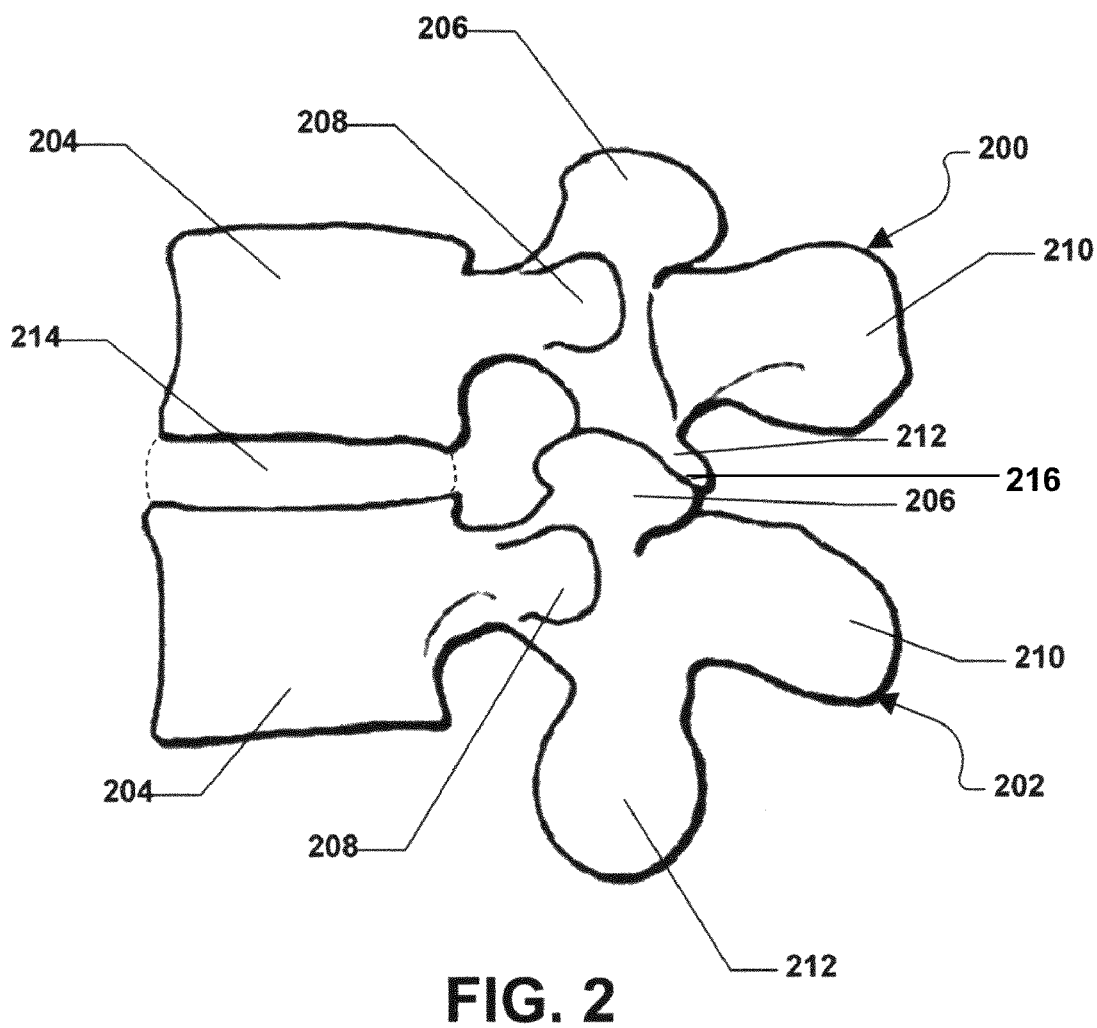
FIG. 2 includes a lateral view of a pair of adjacent vertebrae.

FIG. 2 depicts a detailed lateral view of two adjacent vertebrae, e.g., two of the lumbar vertebrae 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 214 between the superior vertebra 200 and the inferior vertebra 202. A zygapophyseal joint 216 is located between the inferior articular process 212 of the superior vertebra 200 and the superior articular process 206 of the inferior vertebra 202. As described in greater detail below, an intervertebral controlled release device according to one or more of the embodiments described herein can be installed within or in proximity to the intervertebral disc 214 between the superior vertebra 200 and the inferior vertebra 202 or within or in proximity to the zygapophyseal joint 216.

Figure 3:
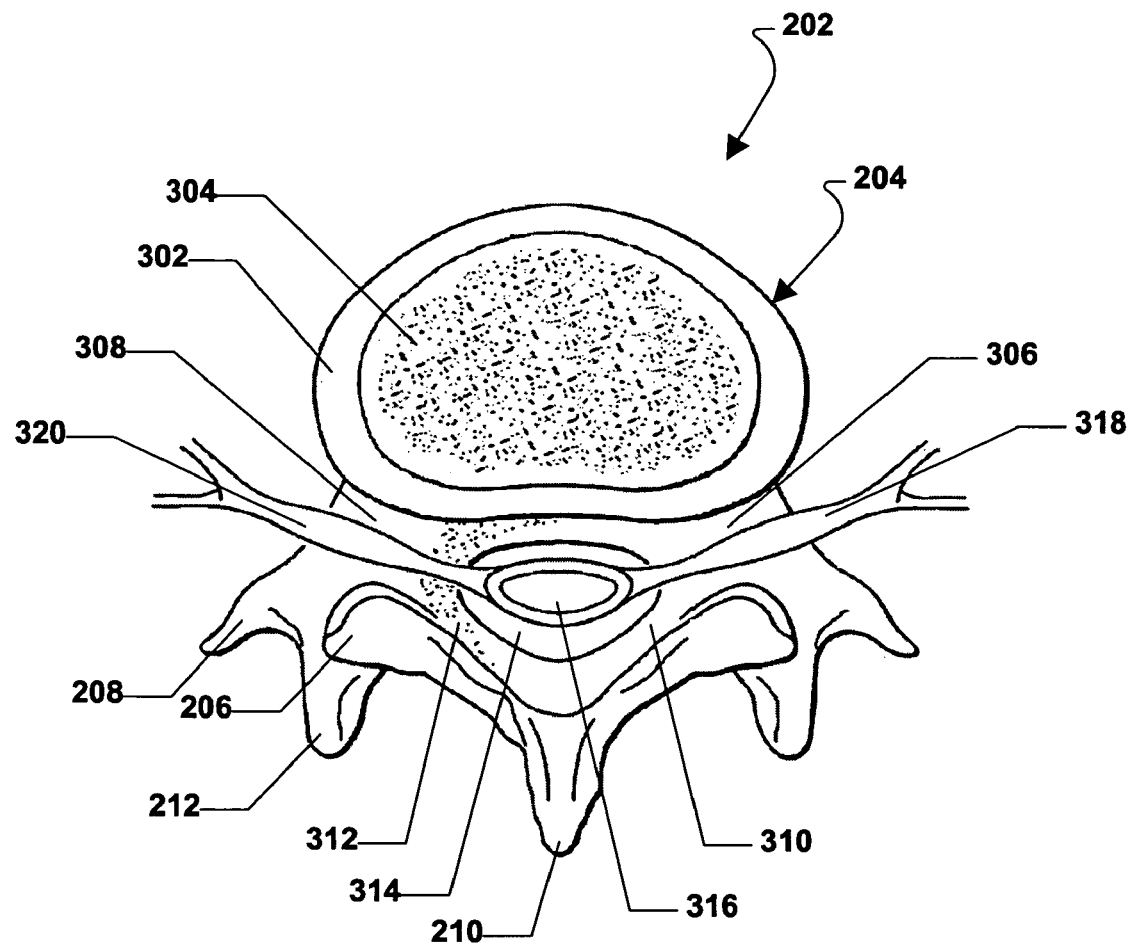
FIG. 3 includes a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is generally softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
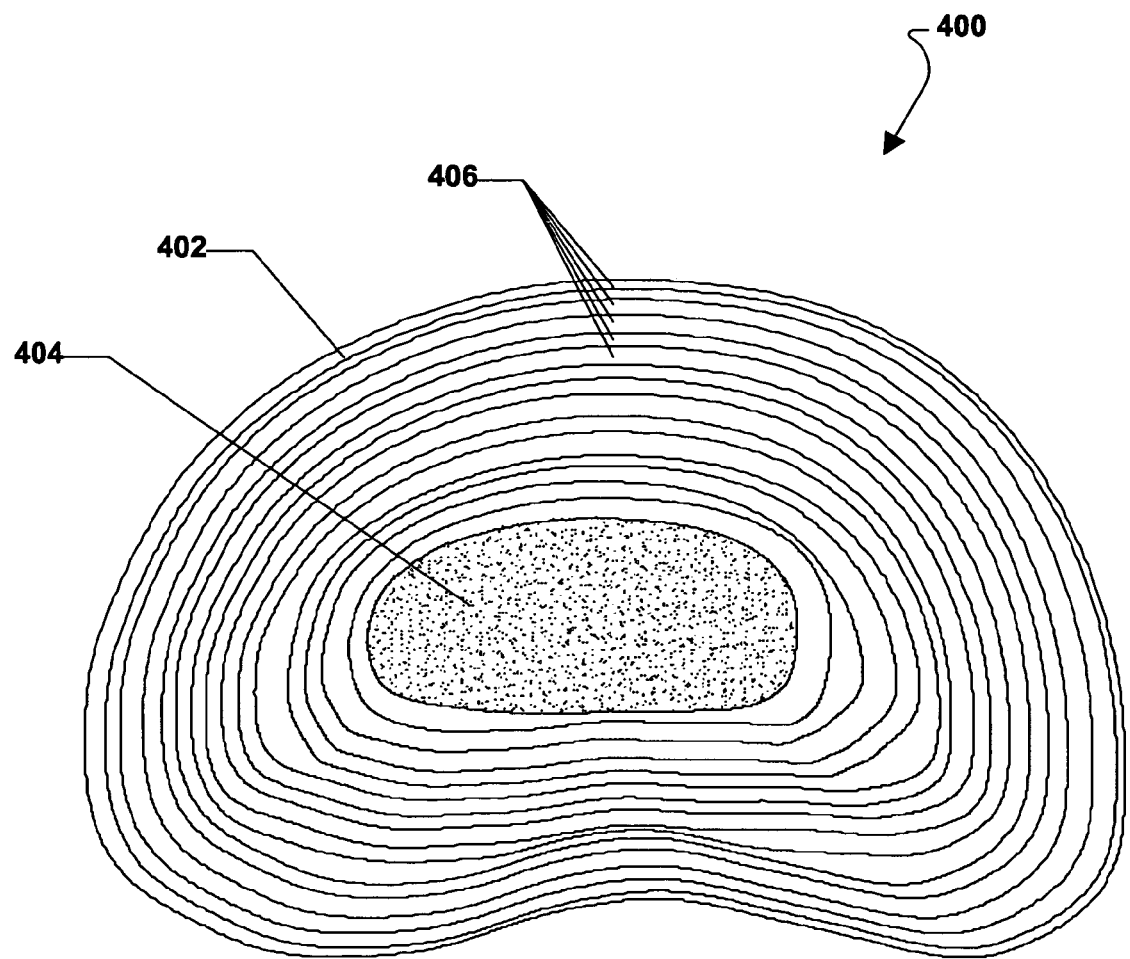
FIG. 4 includes a cross section view of an intervertebral disc.

Referring now to FIG. 4, an intervertebral disc is shown and is generally designated 400. The intervertebral disc 400 is made up of two components: an annulus fibrosis 402 and a nucleus pulposus 404. The annulus fibrosis 402 is the outer portion of the intervertebral disc 400, and the annulus fibrosis 402 includes a plurality of lamellae 406. The lamellae 406 are layers of collagen and proteins. Each lamella 406 includes fibers that slant at 30-degree angles, and the fibers of each lamella 406 run in a direction opposite the adjacent layers. Accordingly, the annulus fibrosis 402 is a structure that is exceptionally strong, yet extremely flexible.

The nucleus pulposus 404 is an inner gel material that is surrounded by the annulus fibrosis 402. It makes up about forty percent (40%) of the intervertebral disc 400 by weight. Moreover, the nucleus pulposus 404 can be considered a ball-like gel that is contained within the lamellae 406. The nucleus pulposus 404 includes loose collagen fibers, water, and proteins. The water content of the nucleus pulposus 404 is about ninety percent (90%) by weight at birth and decreases to about seventy percent by weight (70%) by the fifth decade.

Injury or aging of the annulus fibrosis 402 can allow the nucleus pulposus 404 to be squeezed through the annulus fibers either partially, causing the disc to bulge, or completely, allowing the disc material to escape the intervertebral disc 400. The bulging disc or nucleus material can compress the nerves or spinal cord, causing pain. Accordingly, the nucleus pulposus 404 can be treated with an implantable controlled release device to treat the intervertebral disc 400.

Figure 5:
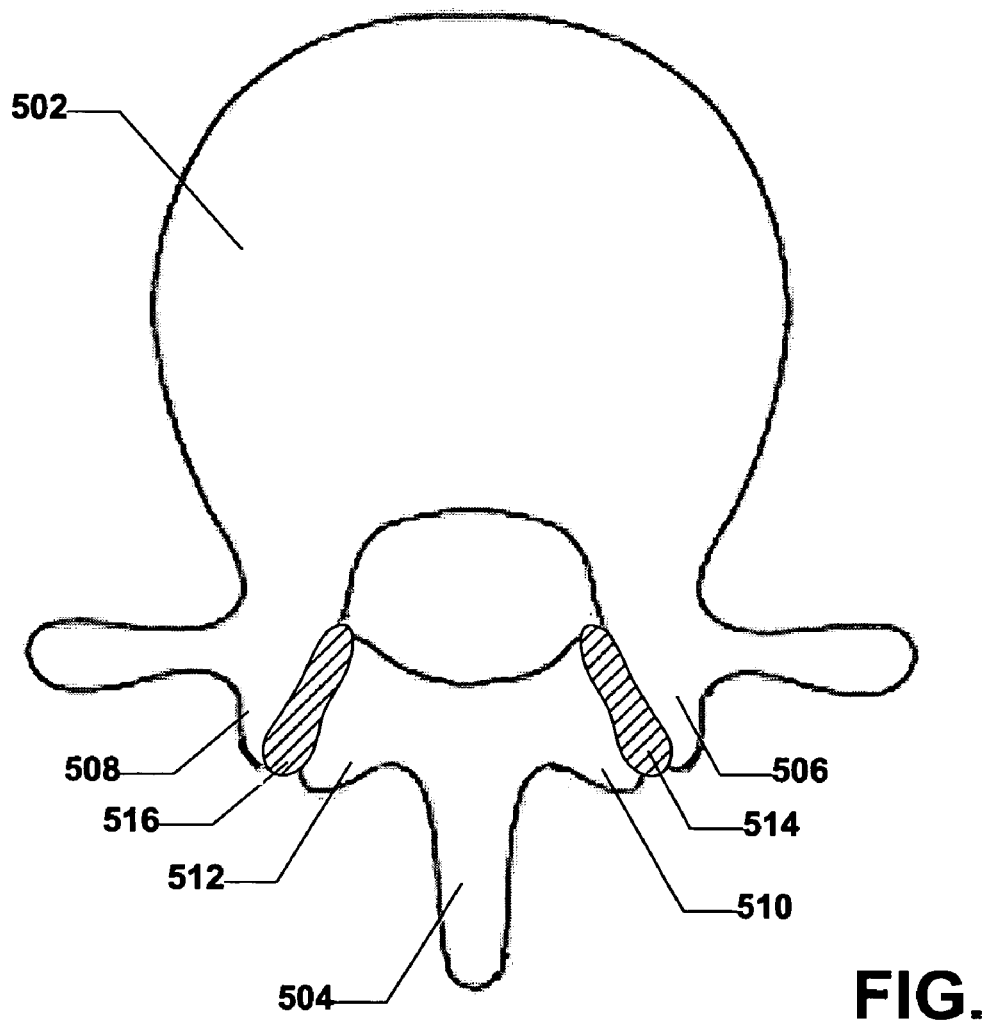
FIG. 5 includes a cross section view of a zygapophyseal joint.

FIG. 5 includes a cross-sectional view of the spine illustrating a portion of a superior vertebra 504 and a portion of an inferior vertebra 502. The inferior vertebra 502 includes superior articular processes 506 and 508 and the superior vertebra 504 includes inferior articular processes 510 and 512. Between the superior articular process 506 and the inferior articular process 510 is a zygapophyseal joint 514 and between the superior articular process 508 and the inferior articular process 512 is a zygapophyseal joint 516.

When damaged or degraded, the zygapophyseal joints 514 and 516 can be treated. For example, an implantable device can be inserted into or in proximity to the zygapophyseal joints 514 and 516. In particular, such an implantable device can be configured to fuse the inferior articular process (506 or 508) to the superior articular process (510 or 512).

Description of Agents

In an exemplary embodiment, a device to be implanted at least partially in the nucleus pulposus of an intervertebral disc or in a zygapophyseal joint includes at least one reservoir to store an agent. The agent can generally affect a condition of the nucleus pulposus or affect bone growth. For example, the agent can decrease the hydration level of a nucleus pulposus or can cause a degeneration of the nucleus pulposus that leads to a reduction in hydration level, to a reduction in pressure, or to a reduction in size of the nucleus pulposus within the intervertebral disc. In another example, the agent can degrade or degenerate a zygapophyseal joint. An agent causing a degeneration of the disc or reduction in hydration level is herein termed a "degradation agent." In another example, an agent (e.g., an osteogenerative agent) can affect bone growth in proximity to the intervertebral disc or the zygapophyseal joint. For example, an osteogenerative agent can be an osteoinductive agent, an osteoconductive agent, or any combination thereof.

An exemplary degradation agent can reduce hydration levels in the nucleus pulposus or can degrade the nucleus pulposus, resulting in a reduction in hydration level or in pressure within the intervertebral disc or the zygapophyseal joint. For example, the degradation agent can be a nucleolytic agent that acts on portions of the nucleus pulposus or on a portion of a zygapophyseal joint. In an example, the nucleolytic agent is proteolytic, breaking down proteins.

An exemplary nucleolytic agent includes a chemonucleolysis agent, such as chymopapain, collagenase, chondroitinase, keratanase, human proteolytic enzymes, papaya proteinase, or any combination thereof. An exemplary chondroitinase can include chondroitinase ABC, chondroitinase AC, chondroitinase ACII, chondroitinase ACIII, chondroitinase B, chondroitinase C, or the like, or any combination thereof. In another example, a keratanase can include endo-β-galactosidase derived from *Escherichia freundii*, endo-β-galactosidase derived from *Pseudomonas* sp. IFO-13309 strain, endo-β-galactosidase produced by *Pseudomonas reptilivora*, endo-β-N-acetylglucosaminidase derived from *Bacillus* sp. Ks36, endo-β-N-acetylglucosaminidase derived from *Bacillus circulans* KsT202, or the like, or any combination thereof. In a particular example, the degradation agent includes chymopapain. In another example, the degradation agent includes chondroitinase-ABC.

An osteogenerative agent, for example, can encourage the formation of new bone ("osteogenesis"), such as through inducing bone growth ("osteoinductivity") or by providing a structure onto which bone can grow ("osteoconductivity"). Generally, osteoconductivity refers to structures supporting the attachment of new osteoblasts and osteoprogenitor cells. As such, the agent can form an interconnected structure through which new cells can migrate and new vessels can form. Osteoinductivity typically refers to the ability of the implantable device or a surface or a portion thereof to induce nondifferentiated stem cells or osteoprogenitor cells to differentiate into osteoblasts.

In an example, an osteoconductive agent can provide a favorable scaffolding for vascular ingress, cellular infiltration and attachment, cartilage formation, calcified tissue deposition, or any combination thereof. An exemplary osteoconductive agent includes collagen; a calcium phosphate, such as hydroxyapatite, tricalcium phosphate, or fluorapatite; calcium sulfate; demineralized bone matrix; or any combination thereof.

In another example, an osteoinductive agent can include bone morphogenetic protein (BMP, e.g., rhBMP-2), demineralized bone matrix; transforming growth factor (TGF, e.g., TGF-β), osteoblast cells, growth and differentiation factor (GDF), LIM mineralized protein (LMP), platelet derived growth factor (PDGF), insulin-like growth factor (ILGF), fibroblast growth factor (FGF), platelet derived growth factor (PDGF), members of the hedgehog family of proteins, interleukins (Ils), colony stimulating factors (CSF), cartilage derived growth factors (CDGF), cartilage derived morphogenetic proteins (CDMP), or any combination thereof. In a further example, an osteoinductive agent can include HMG-CoA reductase inhibitors, such as a member of the statin family, such as lovastatin, simvastatin, pravastatin, fluvastatin, atorvastatin, cerivastatin, mevastatin, pharmaceutically acceptable salts esters or lactones thereof, or any combination thereof. With regard to lovastatin, the substance can be either the acid form or the lactone form or a combination of both. In a particular example, the osteoinductive agent includes a growth factor. In addition, osteoconductive and osteoinductive properties can be provided by bone marrow, blood plasma, or morselized bone of the patient, or other commercially available materials.

In addition, the implantable device can include an anti-inflammatory agent. An exemplary anti-inflammatory agent can include a soluble tumor necrosis factor α-receptor, a pegylated soluble tumor necrosis factor α-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, an inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof. Another exemplary anti-inflammatory agent can include Adalimumab, Infliximab, Etanercept, Pegsunercept (PEG sTNF-R1), Onercept, Kineret®, sTNF-R1, CDP-870, CDP-571, CNI-1493, RDP58, ISIS 104838, 1→3-β-D-glucan, Lenercept, PEG-sTNFRII Fc Mutein, D2E7, Afelimomab, AMG 108, 6-methoxy-2-napthylacetic acid or betamethasone, capsaiein, civanide, TNFRc, ISIS2302 and GI 129471, integrin antagonist, alpha-4 beta-7 integrin antagonist, cell adhesion inhibitor, interferon gamma antagonist, CTLA4-Ig agonist/antagonist (BMS-188667), CD40 ligand antagonist, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-1 0, HuMax IL-15 (anti-IL 15 antibody), or any combination thereof.

In addition, other agents can be incorporated into a reservoir, such as an antibiotic, an analgesic, an anesthetic, a radiographic agent, or any combination thereof. For example, a pain medication can be incorporated within the reservoir in which another agent, such as a degradation agent or an osteogenerative agent, is contained or in a separate reservoir. An exemplary pain medication includes codeine, propoxyphene, hydrocodone, oxycodone, or any combination thereof. In a further example, an antiseptic agent can be incorporated within a reservoir. For example, the antiseptic agent can include an antibiotic agent. In an additional example, a radiographic agent can be incorporated into a reservoir, such as an agent responsive to x-rays.

Each of the agents or a combination of agents can be maintained in liquid, gel, paste, slurry, solid form, or any combination thereof. Solid forms include powder, granules, microspheres, miniature rods, or embedded in a matrix or binder material, or any combination thereof. In an example, fluids or water from surrounding tissues can be absorbed by the device and placed in contact with an agent in solid form prior to release. Further, a stabilizer or a preservative can be included with the agent to prolong activity of the agent.

In particular, one or more agents can be incorporated into a polymeric matrix, such as a hydrogel, a bioresorbable polymer, or a natural polymer. An exemplary hydrogel can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or any combination thereof. An exemplary bioresorbable polymer can include polylactide (PLA), polyglycolide (PGA), poly(lactide-co-glycolide) (PLGA), polyanhydride, polyorthoester, or any combination thereof. An exemplary natural polymer can include a polysaccharide, collagen, silk, elastin, keratin, albumin, fibrin, starch, chitosans, gelatin, alginates, dextrans, or any combination thereof. Other exemplary polymers include poly(alpha-hydroxy acids), conjugates of poly(alpha-hydroxy acids), polyaspirins, polyphosphagenes, PVA-g-PLGA, PEGT-PBT copolymer (polyactive), PEO-PPO-PEO (pluronics), PEO-PPO-PAA copolymers, PLGA-PEO-PLGA, polyphosphoesters, polyester-anhydrides, polyamino acids, polyurethane-esters, polyphosphazines, polycaprolactones, polytrimethylene carbonates, polydioxanones, polyamide-esters, polyketals, polyacetals, glycosaminoglycans, hyaluronic acid, hyaluronic acid esters, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyethylene oxides, polyorthocarbonates, polycarbonates, or copolymers or physical blends thereof or combinations thereof.

Description of a Device

In a particular embodiment, an implantable device can include a reservoir configured to include an osteogenerative agent and a reservoir configured to include a degradation agent. In addition, the implantable device includes a control element connected to at least one of the reservoirs and a reservoir driver connected to at least one of the reservoirs. In particular, the implantable device is configured to release a degradation agent prior to releasing an osteogenerative agent. As a result, adjacent osteal process can fuse.

Figure 6:
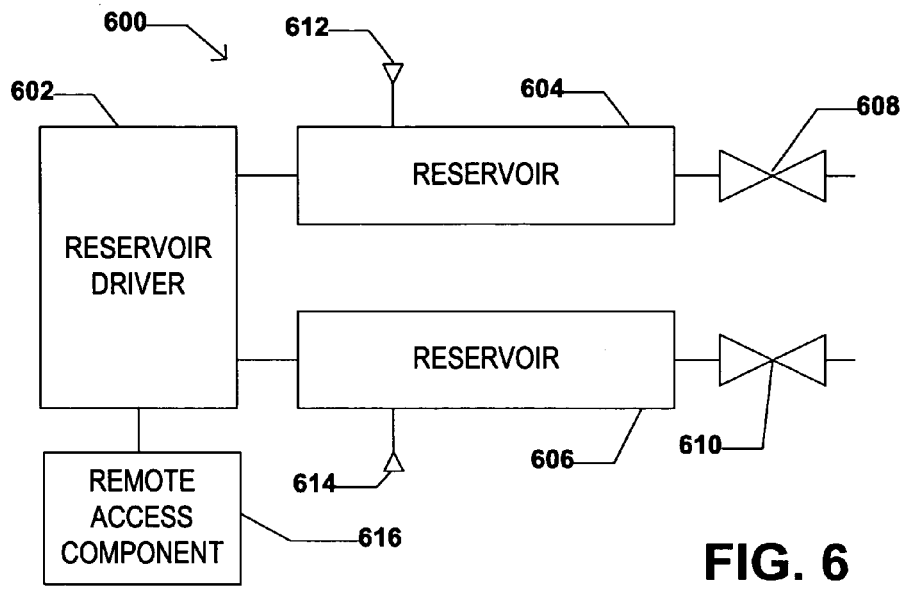
FIG. 6 includes an illustration of an exemplary controlled release device.

FIG. 6 illustrates an exemplary controlled release device 600 to be implanted in a nucleus pulposus of an intervertebral disc. For example, the device 600 can include a reservoir driver 602 connected to a reservoir 604. The reservoir 604 can be configured to include an agent configured to influence a condition of a surrounding tissue, such as a soft tissue, or can be configured to include an agent configured to influence bone growth. In an example, the reservoir 604 can include a degradation agent to degrade or deconstruct a proximate soft tissue. In another example, the reservoir 604 can include an osteogenerative agent.

The reservoir 604 can be connected to a control element 608. For example, the control element 608 can be in fluid communication with the reservoir 604. In an example, the control element 608 can be a valve that opens or closes in response to pressure within the reservoir 604.

In addition, the device 600 can include a reservoir 606. The reservoir 606 can include a second agent, such as an osteogenerative agent or a degradation agent. In another example, the second agent can be a pain medication. The reservoir 606 can be connected to a control element 610 that can open or close in response to pressure within the reservoir 606.

In an exemplary embodiment, the control elements 608 and 610 can be configure to provide access to agents stored in the reservoirs 604 and 606, respectively. For example, the control element (608 or 610) can include a valve that permits fluid agent to exit the reservoir (604 or 606). In another example, the control element (608 or 610) can include a pump that removes fluid agent from the reservoir (604 or 606). In a further example, the control element (608 or 610) can include a door or rotating element that permits solid form agent to be pushed from the reservoir (604 or 606). Below, embodiments are disclosed that include control elements, such as valves. Alternatively, the control elements can be implemented as described in U.S. patent application Ser. No. 11/410,216, entitled "CONTROLLED RELEASE SYSTEMS AND METHODS FOR INTERVERTEBRAL DISCS," filed Apr. 24, 2006, and naming inventor Hai H. Trieu, which is included herein by reference in its entirety.

In an embodiment, the device 600 includes a reservoir driver 602. For example, the reservoir driver 602 can be configured to manipulate a state of a reservoir (604 or 606). In particular, the reservoir driver 602 can be configured to manipulate a state of the reservoir (604 or 606), such as a pressure within the reservoir (604 or 606), in response to a condition of a surrounding tissue. In the illustrated embodiment, a single reservoir driver 602 is illustrated. Alternatively, the device 600 can include a second reservoir driver connected to the second reservoir 606. The second reservoir driver can be configured to respond to conditions in the surrounding environment in a manner different from the first reservoir driver 602. For example, the second reservoir 606 can act to create a different response pressure than the first reservoir 602 in response to conditions of surrounding tissue. In a further embodiment, the device 600 can include more than two reservoirs and can include more than one reservoir driver.

In an exemplary embodiment, the reservoir driver 602 can be connected to the reservoirs 604 and 606. The reservoir driver 602 can be configured to motivate the reservoirs 604 and 606 to expel their respective agents in response to conditions of surrounding soft tissue, such as a nucleus pulposus or a zygapophyseal joint. In an example, the reservoir driver 602 can include a hydraulic fluid to drive pistons associated with each reservoir 604 and 606. In another example, the reservoir driver 602 can include an expanding material, such as an osmotic material, that moves a piston associated with the reservoir 604 and a piston associated with the reservoir 606. For example, the reservoir driver 602 can be configured to apply pressure to a movable barrier between the reservoir driver 602 and at least one of the reservoirs (604 or 606), motivating agent from at least one of the reservoirs (604 or 606).

In a particular embodiment, the reservoir driver 602 can be an osmotic driver. For example, the reservoir driver 602 can include a membrane that is permeable to water or fluids of surrounding tissue. In a particular example, the membrane is sensitive to hydraulic pressure in surrounding tissue and permits fluid to permeate across the membrane in or out of the reservoir driver 602 in response to the hydraulic pressure. In another example, the osmotic driver includes an osmotic agent. For example, the osmotic agent can absorb water based on the hydraulic pressure of the surrounding tissue. An osmotic agent within the reservoir driver 602 can absorb water or fluid from the surrounding tissue and expand or increase pressure within reservoir driver 602. The osmotic agent can include a non-volatile water-soluble osmagent, an osmopolymer that swells on contact with water, or a mixture of the two. An osmotic agent, such as sodium chloride with appropriate lubricants, binders, or viscosity modifying agents, such as sodium carboxymethylcellulose or sodium polyacrylate can be prepared in various forms. Sodium chloride in tablet form is a water swellable agent. In various embodiments, the osmotic agent can generate between about 0 and about 36 MPa (about 5200 psi) of pressure.

Materials suitable for the fluid permeable membrane include those that are semipermeable and that can conform to the shape of the housing upon wetting and make a watertight seal with the rigid surface of the housing. The polymeric materials from which the membrane can be made vary based on the pumping rates and device configuration requirements and can include plasticized cellulosic materials, enhanced polymethylmethacrylate such as hydroxyethylmethacrylate (HEMA), elastomeric materials such as polyurethanes and polyamides, polyether-polyamide copolymers, thermoplastic copolyesters, or the like, or any combination thereof. In a particular example, the osmotic driver has a slow response, effectively responding to an average condition of the surrounding tissue, such as an average pressure condition or an average hydration condition.

In an exemplary embodiment, at least one of the control elements (608 or 610) is configured to respond to pressure within at least one of the reservoirs (604 or 606). For example, the respective control element (608 or 610) can open or close based on the pressure within the respective reservoir (604 or 606). As a result, the respective control element (608 or 610) can open or close based on the condition of the tissue, which influences the reservoir driver 602 that in turn influences the respective reservoir (604 or 606).

In a particular example, at least one of the control elements (608 or 610) can be configured to implement a controlled release strategy (e.g., configured to open or close to pressure within at least one of the reservoirs (604 or 606) based at least in part on the type of agent stored within the respective reservoir (604 or 606)). To simplify the explanation of particular embodiments, the discussion below assumes that the reservoir 604 is configured to include a degradation agent and that the reservoir 606 is configured to include an osteogenerative agent.

Figure 7:
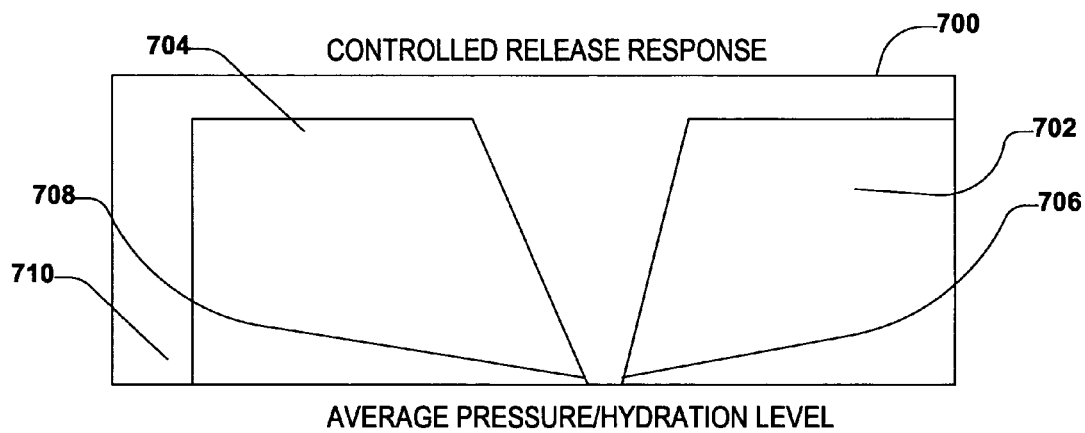
FIG. 7 and FIG. 8 include illustrations of exemplary control strategies.
Figure 8:
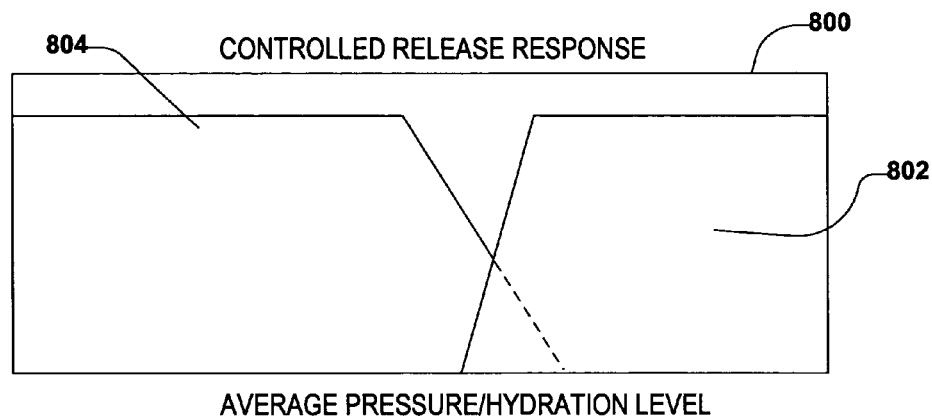

For example, FIGS. 7 and 8 include illustrations of exemplary controlled release strategies. In the example controlled release strategy 700 illustrated in FIG. 7, when the environment surrounding the device 600 has a very low average pressure or low hydration level, as illustrated at 710, no agent is released. Such a condition can exist prior to implanting the device. As such, the control elements, 608 and 610, are closed. As shown in FIG. 7, the control element 610 is configured to open in response to a first soft tissue condition of pressure or hydration and close in response to a second soft tissue condition. The control element 608 is configured to remain closed during the first soft tissue condition and the second soft tissue condition and is configured to open during a third soft tissue condition. The first soft tissue condition is a low pressure or hydration condition as shown at 704. The second soft tissue condition is a pressure or hydration condition higher than the first soft tissue condition as shown in FIG. 7 where the average pressure or hydration level is below the threshold 706 and above the threshold 708. The third soft tissue condition is a pressure or hydration condition higher than the first soft tissue condition and the second soft tissue condition as shown at 702.

When the average pressure or the hydration level of the surrounding tissue is high, such as above a high threshold 706, the device can be configured to release a degradation agent, as illustrated at 702. For example, a control element associated with a reservoir storing degradation agent can be open and a control element associated with an osteogenerative agent can be closed.

When the average pressure or the hydration level of the surrounding tissue is moderate, such as below the threshold 706 and above the threshold 708, the device can be configured to prevent the release of agents. For example, a control element associated with a reservoir storing an osteogenerative agent can be closed and a control element associated with a reservoir storing a degradation agent can be closed.

When the average pressure or the hydration level of the surrounding environment is low, such as below the threshold 708, the device can be configured to release an osteogenerative agent, as illustrated at 704. For example, the device can be configured to release an osteoinductive agent to encourage bone growth and in particular, initiate fusion of adjacent osteal structures. In another exemplary controlled release strategy 800 illustrated in FIG. 8, the control response 802 for the release of degradation agent can overlap with the control response 804 for the release of osteogenerative agent.

To affect such a control strategy, a control element connected to a reservoir including an osteogenerative agent can have two closed positions and a control element connected to a reservoir including a degradation agent can be configured to open at high pressures. For example, if the reservoir 606 includes an osteogenerative agent and the reservoir 604 includes a degradation agent, the control elements 608 and 610 can be configured to implement the controlled release strategy illustrated in FIG. 7. When the reservoir driver is dehydrated, as can be the case as illustrated at 710, the control element 608 and the control element 610 can be closed. When the reservoir driver 602 is hydrated and the device is implanted in situ, the control elements 608 and 610 can have an open or closed state based on the condition of the surrounding tissue. When the surrounding tissue is in conditions as illustrated at 702, the control element 608 can be open and the control element 610 can be closed. When the surrounding tissue is in a condition as illustrated at 704, the control element 608 can be closed and the control element 610 can be open. In addition, the control elements 608 and 610 can be configured to fail closed (i.e., when no pressure exists in the reservoirs (604 or 606), the control elements 608 and 610 are closed).

In an exemplary embodiment, a refill port, such as the refill ports 612 and 614, can be coupled to the reservoir (604 or 606). The refill port (612 or 614) can be used to add an agent to the reservoir (604 or 606) prior to implanting the device, such as during manufacture or during configuration of the device for implanting. In addition, the refill port (612 or 614) can be used to add an agent to the reservoir (604 or 606) after use.

In a further exemplary embodiment, the device 600 can include a remote access component 616. The remote access component 616, for example, can couple to the reservoir driver 602. In an example, the remote access component 616 can respond to a magnetic field. In another example, the remote access component 616 can respond to an electromagnetic signal, such as a radio frequency signal. In a further example, the remote access component 616 can respond to a light signal, such as an infrared signal. In an additional example, the remote access component 616 can respond to a wave signal, such as an ultrasonic signal. In response to a signal from a location external to a patient, the remote access component 616 sends an electrical signal to the reservoir driver 602. In another example, the remote access component 616 can respond to a first oscillating frequency with a first response and can respond to a second oscillating frequency with a second response. The first response can be communicated to a first reservoir driver and the second response can be communicated to a second reservoir driver.

In a particular example, the remote access component 616 can include at least one induction coil. When an oscillating field induces current within the coil, the reservoir driver 602 can adjust, influencing the pressure within one or more reservoirs (604 or 606). In a further example, the device 600 can include more than one reservoir driver 602. For example, the device 600 can include an osmotic reservoir driver and an electro-mechanical reservoir driver activated by the remote access component 616. In a particular example, a single reservoir can be connected to an osmotic driver and an electro-mechanical driver.

The device, such as device 600 illustrated in FIG. 6, can be included in a housing. The housing can form a cylinder, sphere, capsule, disc, cone, coil shape, or any combination thereof. In an example, the housing can surround each of the components of the device. Alternatively, the individual components can be included within one or more housings.

The housing can be configured based on the soft tissue in which the device is to be implanted. In particular, the smallest dimension of the housing can be configured to fit between osteal structures in proximity to the soft tissue. For example, when the soft tissue includes an intervertebral disc, the dimensions of the housing can be configured to fit between the superior and the inferior vertebrae. In another example, when the soft tissue includes a zygapophyseal joint, the housing can be configured to fit between articular processes of adjacent vertebrae. In an example, the housing can have a smallest dimension not greater than about 8 mm. For example, the smallest dimension can be not greater than about 5 mm, such as not greater than about 3 mm. In a particular example, a cylindrical housing can have a diameter that is not greater than about 8 mm. In an exemplary capsule-shaped housing, the diameter around the center is not greater than about 8 mm.

The housing can be formed of a metallic material, a polymeric material, or any combination thereof. An exemplary polymeric material can include polypropylene, polyethylene, halogenated polyolefin, fluoropolyolefin, polybutadiene, polysulfone, polyaryletherketone, polyuerethane or compolyers thereof, silicone, polyimide, polyamide, polyetherimide, a hydrogel, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

Figure 9:
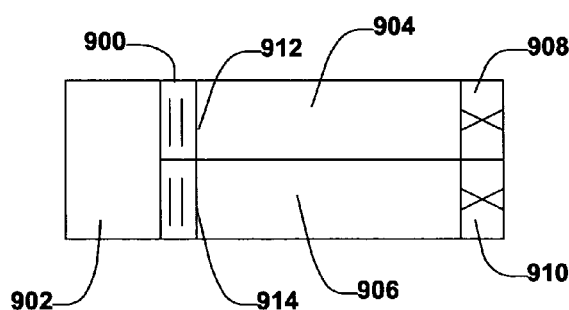
Figure 10:
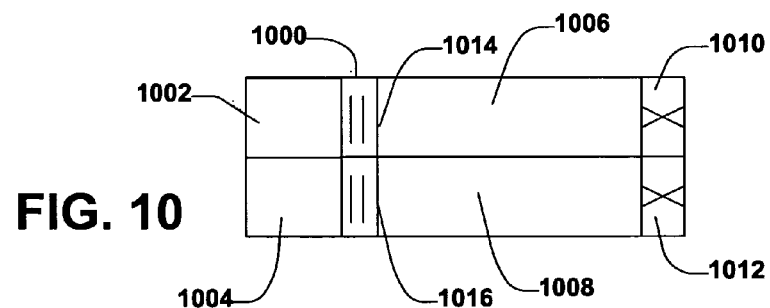

FIG. 9, FIG. 10, FIG. 11, FIG. 12, FIG. 13, FIG. 14, FIG. 15, and FIG. 16 include illustrations of exemplary embodiments of a controlled release device. For example, FIG. 9 and FIG. 10 illustrate a side-by-side configuration of a two-reservoir device. FIG. 9 illustrates an exemplary device 900 including a single reservoir driver 902 connected by movable barriers 912 and 914 to reservoirs 904 and 906, respectively. The reservoir driver 902 can impart pressure through the barrier 912 and 914 to influence the pressure of the reservoirs 904 and 906 respectively. In response to the pressure of the reservoirs 904 and 906, valves 908 and 910, respectively, can open or close. FIG. 10 illustrates an exemplary device 1000 that includes two reservoir drivers 1002 and 1004. The reservoir driver 1002 can act through movable barrier 1014 to influence the pressure of reservoir 1006, which in turn influences the position of a valve 1010. The reservoir driver 1004 can act through movable barrier 1016 to influence the pressure of reservoir 1008, which in turn influences the position of a valve 1012.

Figure 11:
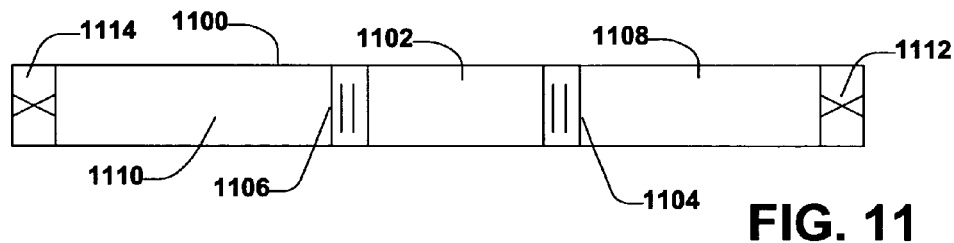
Figure 12:
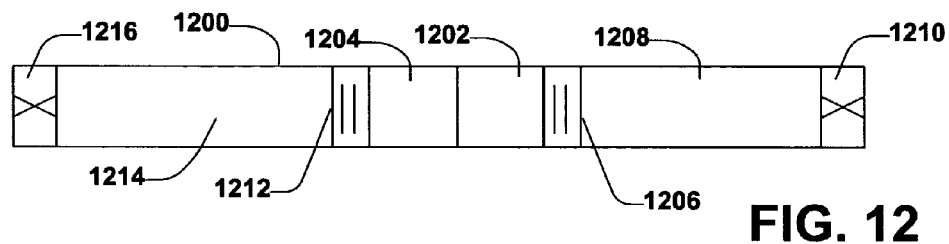

FIG. 11 and FIG. 12 include illustrations of another configuration of a two-reservoir device. For example, FIG. 11 illustrates a device 1100 in which a single reservoir driver 1102 can expand in opposite directions to influence the pressure in reservoirs 1108 and 1110. For example, the reservoir driver 1102 can expand in a first direction, moving the barrier 1104 to influence the pressure in reservoir 1108, which in turn influences the position of the valve 1112. In addition, the reservoir driver 1102 can act in a second direction opposite the first direction, moving the barrier 1106 to influence the pressure in the reservoir 1110, which in turn influences the position of the valve 1114. FIG. 12 includes an illustration of a two-reservoir driver embodiment 1200. For example, the reservoir driver 1202 can act in a first direction to move the barrier 1206 to influence the pressure in the reservoir 1208 and the position of the valve 1210. In addition, the reservoir driver 1204 can act in a second direction opposite the first direction to move the barrier 1212 to influence the pressure in the reservoir 1214 and the position of the valve 1216.

Figure 13:
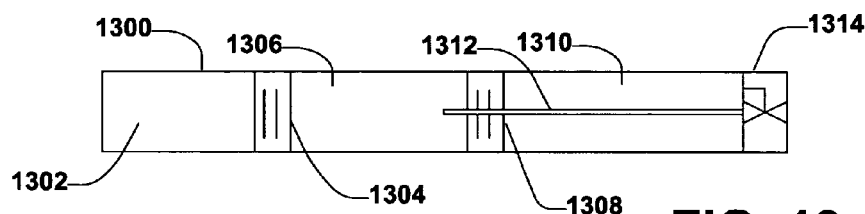

In a further exemplary embodiment, FIG. 13 illustrates a device 1300 including aligned reservoirs. For example, a reservoir driver 1302 can act on a movable barrier 1304 to influence the pressure in reservoir 1306. The pressure in reservoir 1306 can act on the movable barrier 1308 to influence the pressure of the reservoir 1310. A fluid channel 1312 can connect the reservoir 1306 to the valve assembly 1314. In an exemplary embodiment, the valve assembly 1314 includes a three-way valve. In another example, the valve assembly 1314 includes two valves. The exemplary devices (1100, 1200, and 1300) of FIG. 11, FIG. 12, and FIG. 13, can be housed in a cylindrical housing.

Figure 14:
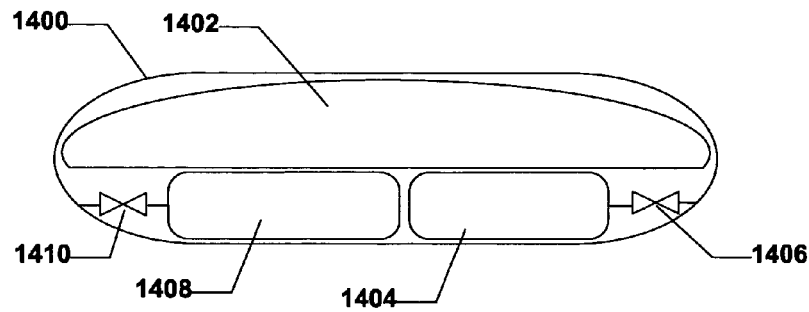

In another exemplary embodiment, a capsule shaped housing or a disc-shaped housing can be used. FIG. 14 illustrates a device 1400 that includes a reservoir driver 1402 overlying a reservoir 1408 and a reservoir 1404. The valves 1406 and 1410 can be connected to the reservoirs 1404 and 1408, respectively. In the exemplary embodiment illustrated in FIG. 14, a larger surface area of the device 1400 can be used for fluid transfer into and out of the reservoir driver 1402 than in other configurations described above.

In a further exemplary embodiment, FIG. 15 illustrates a device 1500 including a second reservoir driver 1510 attached to a reservoir 1506. For example, a reservoir driver 1502 can act on a movable barrier 1504 to influence the pressure in the reservoir 1506 as described above in relation to other embodiments. The second reservoir driver 1510 can act on the reservoir 1506 via barrier 1508. For example, the second reservoir driver 1510 can act to increase the pressure of the reservoir 1506 in response to a signal from a remote access component 1516. An exemplary remote access component can include an induction coil or a circuitry responsive to signals, such as radiofrequency signals, infrared signals, ultrasonic signals, or any combination thereof. A fluid channel 1512 can connect the reservoir 1506 to the valve assembly 1514, which responds to the pressure in the reservoir 1506. In an alternative embodiment, the device 1500 can include one or more additional reservoirs and one or more additional drivers. For example, an implanted device 1500 can act to release agent in response to a signal from a device external to the patient. In an example, a healthcare provider can perform a scan, such as a CT scan or an MRI scan, to determine a condition of an intervertebral disc or a zygapophyseal joint. Based on the results of the scan, the healthcare provider can activate the device via the remote access component to adjust the release of agents.

In a further exemplary embodiment illustrated in FIG. 16, an implantable device 1602 can include a structure 1604 configured to expand or extend. Such a structure 1604 can include a surface of the implantable device 1602 or can include a particular element of the device 1602. In particular, the structure 1604 can extend to engage an adjacent osteal structure, such as a process or vertebral body.

The device 1602 can include a mechanism to extend or expand the structure 1604. For example, the device can include a flexible container configured to expand when fluid, such as a gas or liquid is introduced. In particular, a fluid can be introduced into the device 1602 during implantation to extend the structure 1604 to a desired extension. In another example, the mechanism can be an osmotic device configured to expand in response to absorbed liquid from surrounding tissue, extending the structure 1604 to a configured extension. In a further example, the mechanism can include a screw device, an electrically driven device, or a wedge device. In particular, a wedge or solid component can be inserted into the device during the implanting process to extend the structure 1604.

For example, the structure 1604 can be extended to engage one or more osteal structures, such as vertebral bodies or processes. In such a manner, the device can be secured in place. In addition, the structure 1604 can act to encourage bone growth and can be osteoconductive.

In a particular embodiment, the device 1602 can include a textured surface. Such a textured surface can be configured to secure the device to an osteal structure. In particular examples illustrated in FIG. 17 and in FIG. 18, an implantable device can have a surface, such as surface 1702 or surface 1802, with structures 1704 or serrations 1804. In an example, the structures 1704 or serrations 1804 can engage an osteal structure. In another example, the structures 1704 or serrations 1804 can irritate a soft tissue, such as a vertebral cartilagenous end cap, to further affect bone growth. Alternatively, a textured surface can be osteoconductive. For example, the structure 1604 can include osteogenerative material, including a bone graft, a bone graft substitute, a bone growth factors/carrier, an allograft, an autograft, or any combination thereof.

Figure 24:
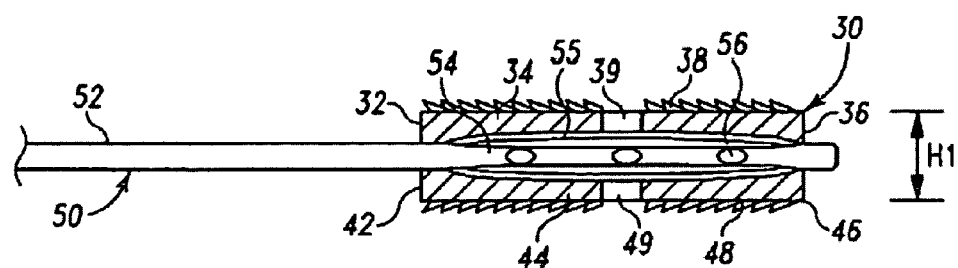
FIG. 24, FIG. 25, FIG. 26, FIG. 27, and FIG. 28 include illustrations of exemplary expandable components.
Figure 25:
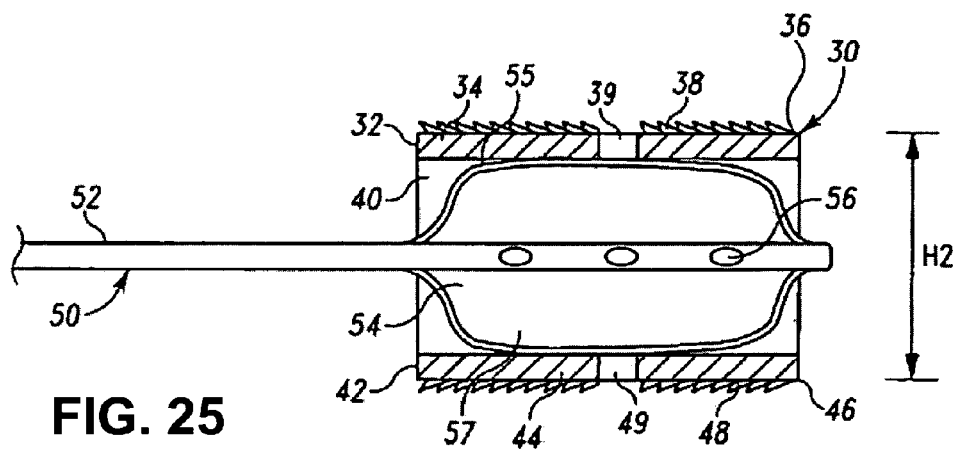

A further embodiment of an expandable mechanism 30 is illustrated in FIG. 24 and FIG. 25. In this embodiment, the expandable mechanism 30 can include an elongated body positionable in a spinal disc space that includes a first portion 34 positionable along one endplate of a first vertebra and a second portion 44 positionable along the endplate of an adjacent second vertebra. The first portion 34 can extend between a distal leading insertion end 36 and a proximal trailing end 32. The second portion 44 can extend between a distal leading insertion end 46 and a proximal trailing end 42. A cavity 40 can be defined between the first portion 34 and the second portion 44. The cavity 40 can extend between and open at the distal end 36 and the trailing end 32.

The first portion 34 can be provided with a number of protrusions 38, and the second portion 44 also can be provided with a number of protrusions 48. The protrusions 38, 48 can be configured to engage bony tissue of the vertebrae, and can be in the form of teeth, spikes, ridges, threads, barbs, knurlings, fins, and combinations thereof, for example. Alternatively, the outer surfaces can be smooth, or auxiliary fixation or engagement members can be provided. The first and second portions 34, 44 can further include one or more openings 39, 49, respectively, to facilitate bone growth.

The first portion 34 and the second portion 44 are movable away from one another from an unexpanded configuration, as illustrated in FIG. 24, to an expanded configuration, as illustrated in FIG. 25. In the unexpanded configuration, the expandable mechanism 30 has a height H1 between the first portion 34 and the second portion 44. In the expanded configuration, the expandable mechanism 30 has a height H2 between the first portion 34 and the second portion 44. The height H1 can allow the expandable mechanism 30 to be inserted, for example, in a disc space between adjacent vertebral bodies. The height H2 can correspond to a separation height between the first and the second portions 34, 44 to provide a desired disc space height between adjacent vertebrae.

A delivery instrument 50 can be provided to move the expandable mechanism 30 from its unexpanded configuration to its expanded configuration. The delivery instrument 50 can include a proximal shaft 52 and a distal portion 54 including an expandable element 55. In the illustrated embodiment, expandable element 55 is an inflatable balloon-like structure having a collapsed configuration, as illustrated in FIG. 24, and an enlarged, inflated configuration, as illustrated in FIG. 25. The shaft 52 can be provided with a lumen through which fluid or material can be supplied through openings 56 to an internal volume 57 of the expandable element 55 to enlarge or inflate the expandable element 55. The expandable element 55 can be positionable in the cavity 40 of the expandable mechanism 30 with each of the expandable element 55 and the expandable mechanism 30 in its unexpanded or collapsed configuration.

After delivery of the expandable mechanism 30 to the operative site, the expandable element 55 can be inflated to provide an enlarged configuration for the expandable element 55 and thus, separate the first and second portions 34, 44 of the expandable mechanism 30. As the expandable mechanism 30 is expanded, the first portion 34 and the second portion 44 move away from one another and the volume of the cavity 40 is increased. The expansion can distract adjacent vertebra to provide a desired spacing between the adjacent endplates and to restore a disc space height.

An example of a suitable delivery instrument 50 includes a high-pressure balloon catheter. The shaft 52 can be rigid, semi-rigid, or flexible. The shaft 52 can be fabricated from metals, polymers, or combinations thereof. The shaft 52 can be provided with at least one lumen to allow inflation or enlargement of the expandable element 55 with a biocompatible fluid, such as air or saline, for example. In another example, the shaft 52 includes multiple lumens to, for example, deliver bone graft, bone growth material or other suitable filler material into the expanded cavity 40 of an expanded mechanism 30. The expandable element 55 can be collapsed prior to or simultaneously with placement of the filler material.

In the illustrated embodiment, the distal portion 54 includes a single expandable element 55, although multiple expandable elements are also contemplated to provide the distal portion 54 with alternate enlargement characteristics. For example, the distal portion 54 can include a distal expandable element and a proximal expandable element having differing heights to provide angulation between the expanded first and second portions 34, 44 of the expandable mechanism 30. In another example, the distal portion 54 can include an upper expandable element and a lower expandable element which can be selectively expanded to move the adjacent one of the first and second portions 34, 44 while the other of the first and second portions remains stationary. In a further example, the expandable element 55 can expand uni-directionally to move the adjacent one of the first and second portions 34, 44 in the direction of expansion.

In another embodiment, the distal portion 54 can be severed from the shaft 52 after expansion, and post-operatively maintain the expandable mechanism 30 in an expanded condition. Accordingly, the expandable element 55 can be inflated with bone growth material or other suitable filler material to facilitate bone growth or preserve motion of the intervertebral space through the expanded mechanism 30. When the filler material suitably hardens in the expandable element 55 to prevent flow from extending therefrom, the shaft 52 can be removed. Alternatively or additionally, a valve arrangement can be provided adjacent expandable element 55 to prevent the filler material from exiting therefrom. The expandable element 55 can be fabricated from porous material, resorbable material, or other suitable material to allow bone growth through the cavity of the expanded device. In a further embodiment, the expandable element 55 is inflated with a polymer that is flowable into the expandable element and thereafter polymerizes to form an elastic core between the first and second portions 34, 44.

The expandable element 55 can include a size and shape that matches the size and shape of the cavity 40 in its expanded configuration, although non-matching configurations are also contemplated. In the expanded configuration, the expandable element 55 can apply a uniform expansion force along the inner wall surfaces of first portion 34 between leading end 36 and trailing end 32. If configured for bi-directional expansion, the expandable element 55 can apply a uniform expansion force along the second portion 44 between leading end 46 and trailing end 42. The uniform expansion force distributes the distraction loads along the adjacent vertebral endplate to provide uniform distraction along the length of expandable mechanism 30. The expandable element 55 or the cavity 40 can be provided with any suitable overall shape including conical, frusto-conical, spherical, cubic, spherical, polygonal, ovoid, long conical, long spherical, rectangular, tapered, stepped, dog-bone shape, offset shapes and combinations thereof.

The expandable element 55 can be made from any suitable material capable of withstanding the pressure supplied to enlarge or inflate expandable element 55 in situ. An exemplary material includes a polymeric material, such as polyethylene terephthalate, polyolefin, polyurethane, nylon, polyvinyl chloride, silicone, or any combination thereof.

Figure 26:
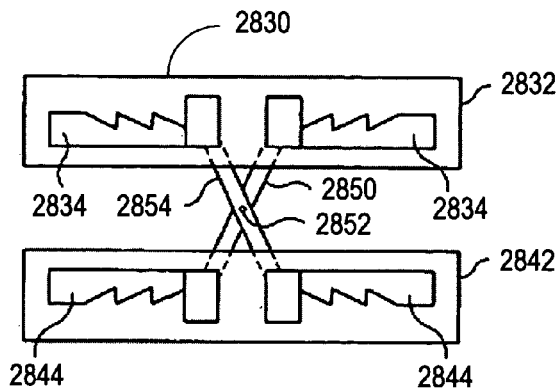

In another exemplary embodiment illustrated in FIG. 26, the expandable mechanism 2830 can include a first portion 2832 and a second portion 2842. Linkages 2850 can movably couple the first and second portions 2832, 2842 to one another and can include first and second members 2852, 2854 pivotally coupled to one another. The members 2852, 2854 each can include a first end positioned in respective ones of receptacles 2834 of first portion 2832, and opposite second ends positioned in respective receptacles 2844 of second portion 2842. The ends of the members 2850, 2852 can include a configuration that interdigitates with a ratchet surface formed along the respective receptacles 2834, 2844.

In the unexpanded configuration, the ends of members 2852, 2854 are positioned at the outer ends of the respective receptacles 2834, 2844. As the first and second portions 2832, 2842 are bi-directionally moved away from one another, the ends of members 2850, 2852 can move longitudinally toward one another along the receptacles 2834, 2844 of each of the respective first and second portions 2832, 2842, as illustrated in FIG. 26. The rigid members 2852, 2854 can move the first and second portions 2832, 2842 away from one another, and engage the ratchet surfaces along receptacles 2834, 2844 to maintain the expanded or separated position between the first and second portions 2832, 2842. Accordingly, the expandable device 2830 is vertically collapsible to facilitate insertion in a collapsed disc space with the delivery instrument, and thereafter vertically expandable to distract the disc space and maintain distraction post-operatively.

Figure 27:
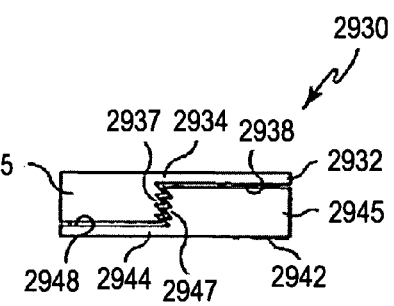

In another example of an expandable mechanism illustrated in FIG. 27, expandable mechanism 2930 includes a first portion 2932 and a second portion 2942. The first portion 2932 includes sidewalls 2934 that each can include an arm 2935. A receptacle 2938 is formed along one end of the arm 2935. The arm 2935 includes engagement surfaces 2937 extending along receptacle 2938. A second portion 2942 similarly includes sidewalls 2944 that each can include an arm 2945 and a receptacle 2948. The arm 2945 can be received in receptacle 2938, and the arm 2935 can be received in receptacle 2948. The arm 2945 can include engagement surfaces 2947 extending therealong that are engageable with the adjacent engaging surfaces 2937 of the arm 2935 of first portion 2932. The engagement surfaces 2937, 2947 can interdigitate and engage one another to maintain the expandable mechanism 2930 in an expanded condition.

Figure 28:
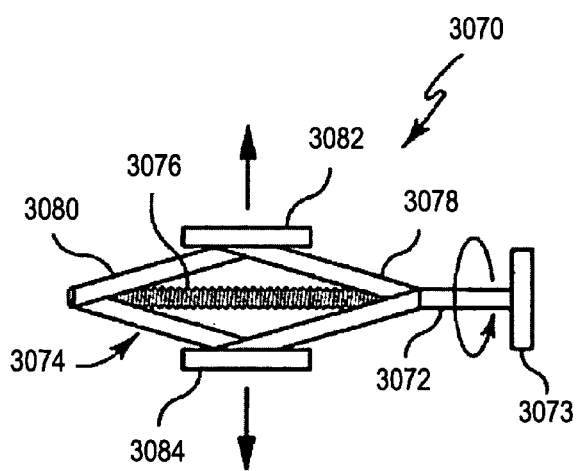

In a further example illustrated in FIG. 28, an expandable mechanism 3070 can include a shaft 3072 that can include a proximal handle portion 3073 and a distal portion 3076 extending through the expandable element 3074. The expandable element 3074 can include a first pivoting linkage 3078 and a second pivoting linkage 3080. The linkages 3078, 3080 each can include an intermediate pivot point engaged to and movable with the distal portion 3076. The linkages 3078, 3080 further can include distraction members 3082, 3084 coupled at the upper and lower ends thereof. The distal portion 3076 can be coupled to linkages 3078, 3080 so that, as the shaft 3072 is rotated about its axis with handle portion 3073 as indicated in FIG. 28, the pivoting intermediate portions of the linkages 3078, 3080 are drawn toward one another to move the distraction members 3082, 3084 away from one another.

Figure 29:
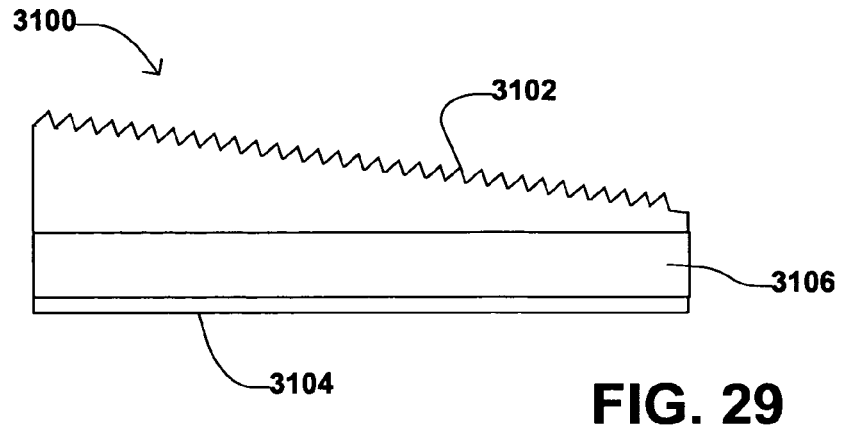
FIG. 29 and FIG. 30 include illustrations of exemplary spacer devices.
Figure 30:
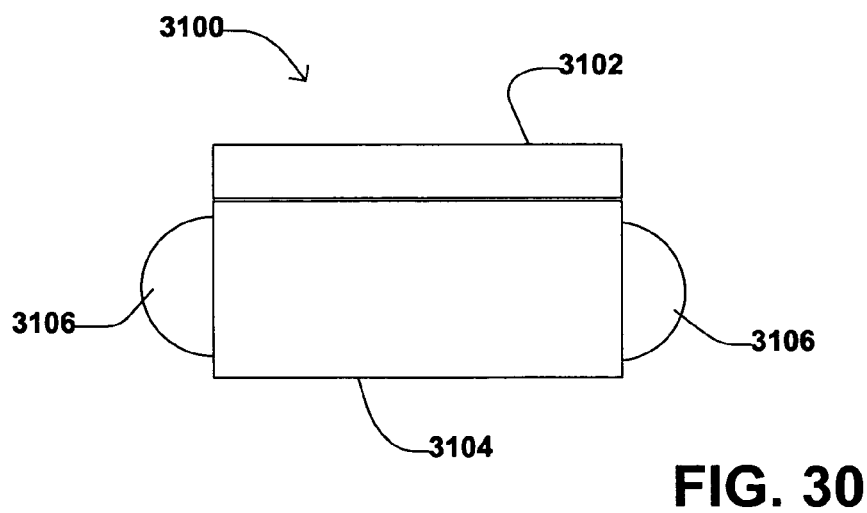

In another example illustrated in FIG. 29 and FIG. 30, the device 3100 can form a spacer. For example, the device 3100 can include surfaces 3102 and 3104 to engage a superior and an inferior vertebrae. In an example, the surface 3102 can include serrations or texture to engage the vertebrae. In another example, the surface 3104 can be smooth. Alternatively, the surfaces 3102 and 3104 can be smooth, textured, or serrated. In addition, the device 3100 can include reservoirs 3106 that extend along an edge of the device 3100. While the device 3100 is illustrated as a wedge, the device 3100 can be configured to have a rectangular, other polygonal, or circular cross-section, or any combination thereof. In a particular example, the device 3100 can have a height of about 0.5 mm to about 4 mm for a zygapophyseal joint implant or can have a height of about 5 mm to about 17 mm for a intervertebral disc implant.

Alternatively, the implantable device can be used in conjunction with other immobilizing devices. For example, the implantable device can be used in conjunction with a screw, a rod and screw system, a separate spacer, a separate fusion cage, interior plate, interspinous spacer, or any combination thereof. In particular, an implantable device can be inserted into an intervertebral disc or one or both of the zygapophyseal joints and the zygapophyseal joints can further be secured with screws. In another example, implantable devices can be used in conjunction with a rod and screw system, such as a percutaneous rod system, for example, a SEXTANT® system, available from Medtronic Sofamor Danek. In a further example, the implantable device can be implanted with a resorbable spacer.

Figure 19A:
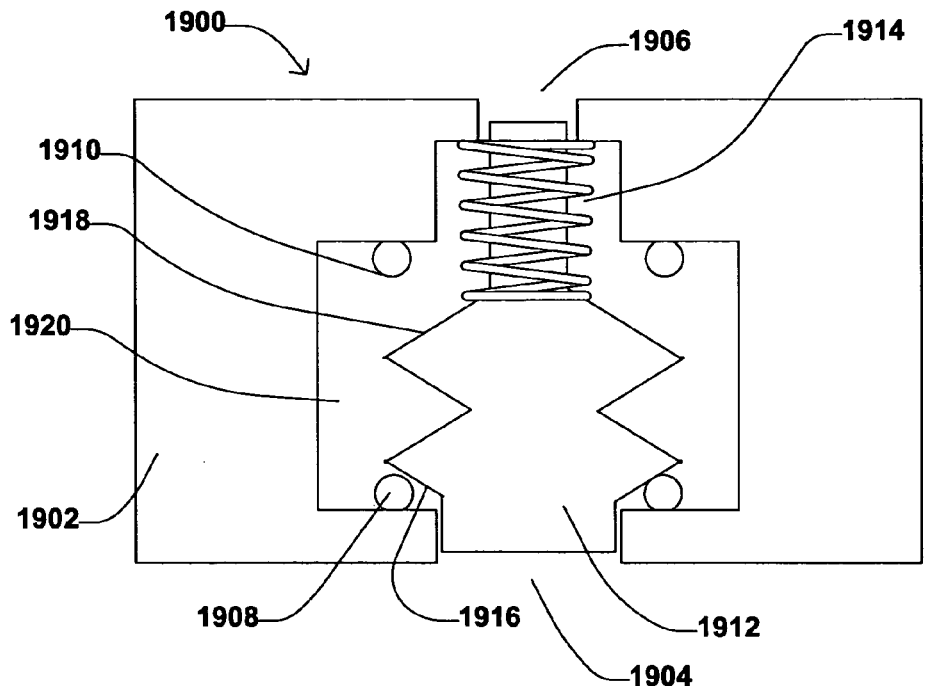
FIG. 19a, FIG. 19b, FIG. 19c, FIG. 20a, and FIG. 20b include illustrations of exemplary valves.
Figure 19B:
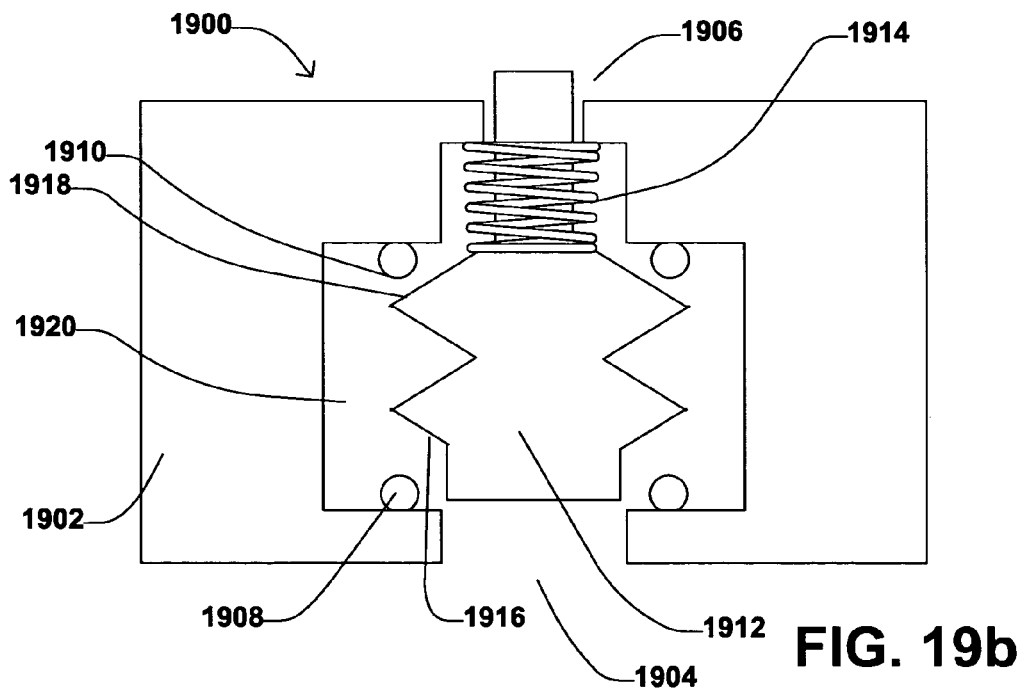
Figure 19C:
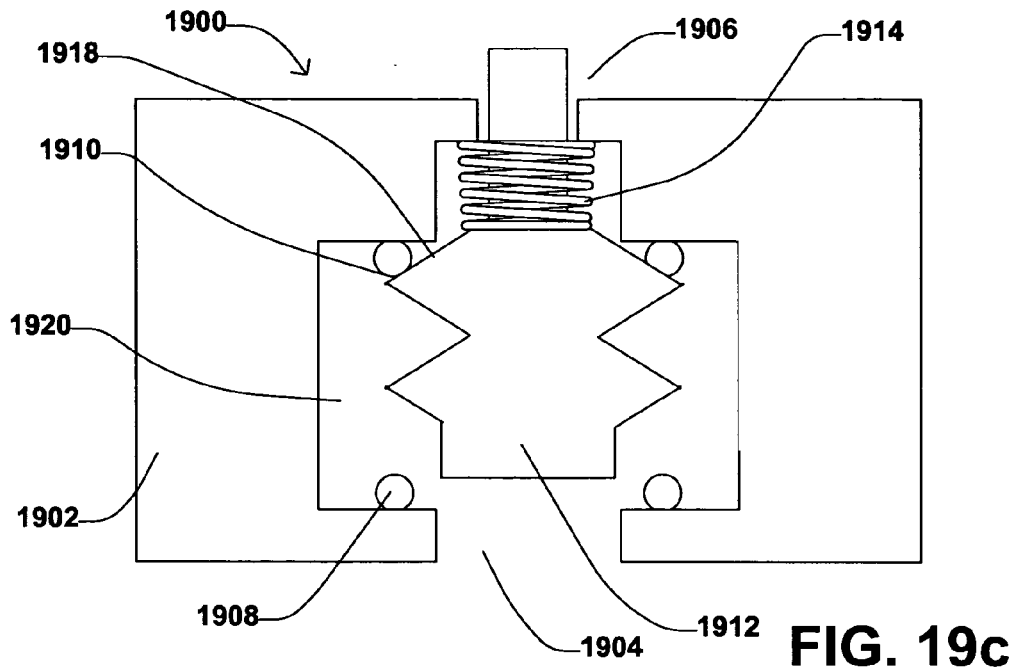

To implement a control strategy, valves coupled to reservoirs can be configured to behave in a manner that correlates with the control strategy. For example, a valve coupled to a reservoir including an osteogenerative agent can be configured to open in response to a specific range of low average pressure or low tissue hydration and close at other times. In a particular example, a valve coupled to a reservoir storing an osteogenerative agent can be configured to have two closed positions. FIG. 19a, FIG. 19b, and FIG. 19c illustrate an exemplary valve 1900, which can have a valve body 1902, a stem 1912, and a spring 1914. The valve body 1902 can include an opening 1904 in communication with a reservoir and an opening 1906 configured to be an effluent opening. The valve body 1902 also can include a chamber 1920 in communication with the openings 1904 and 1906, forming a fluid path therethrough. In addition, the valve 1900 can include a first valve seat 1908 proximate to the valve opening 1904 and a second valve seat 1910 opposite the first valve seat 1908.

In an exemplary embodiment, the valve body 1902 can be formed of metallic material, a polymeric material, or any combination thereof. An exemplary polymeric material can include polypropylene, polyethylene, halogenated polyolefin, fluoropolyolefin, polybutadiene, polysulfone, polyaryletherketone, polyuerethane or compolyers thereof, silicone, polyimide, polyamide, polyetherimide, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

The valve stem 1912 can form a first seal 1916 configured to engage the first valve seat 1908 and a second seal 1918 configured to engage the second valve seat 1910. The valve stem 1912 can be formed as a single integrated part or can be formed of multiple attached parts. In an example, the valve stem can be formed of metallic material, a polymeric material, or any combination thereof. An exemplary polymeric material can include polypropylene, polyethylene, halogenated polyolefin, fluoropolyolefin, polybutadiene, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

In an exemplary embodiment, the spring 1914 can surround a portion of and engage the valve stem 1912 to provide a motivating force in a direction away from the effluent opening 1906 and toward the inlet opening 1904. In an example, the spring 1914 can be a helical compression spring and can be formed of a resilient metal or polymer.

As illustrated at FIG. 19a, the valve spring 1914 can press the valve stem 1912 toward the inlet opening 1904. When the pressure in the reservoir is low, the seal 1916 of the valve stem 1912 can press against the valve seat 1908. As the pressure within the reservoir increases, the force against the valve stem 1912 can increase to counteract the force of the spring 1914. As illustrated at FIG. 19b, a sufficient pressure within the reservoir results in an unseating of the seal 1916 from the valve seat 1908, resulting in a passage through the opening 1904, the chamber 1920, and the opening 1906. As the pressure further increases, the seal 1918 of the valve stem 1912 can press against the valve seat 1910, closing the passage and preventing further agent flow, as illustrated in FIG. 19c. In a particular embodiment, such a valve can remain closed when the device is not in service, can open in response to a low average pressure or low hydration condition in a surrounding tissue, and can be closed based on other conditions in a surrounding tissue. In another exemplary embodiment, the valve can be used in conjunction with an osteogenerative agent and can open during intermediate conditions of surrounding tissue, while closing during other conditions.

Figure 20A:
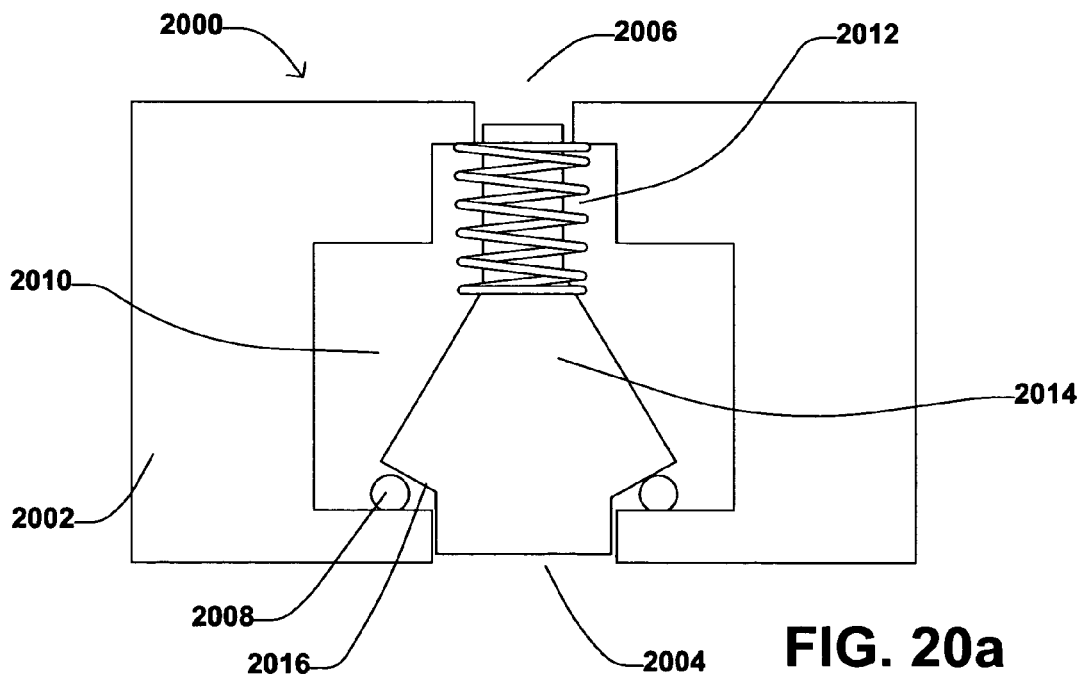
Figure 20B:
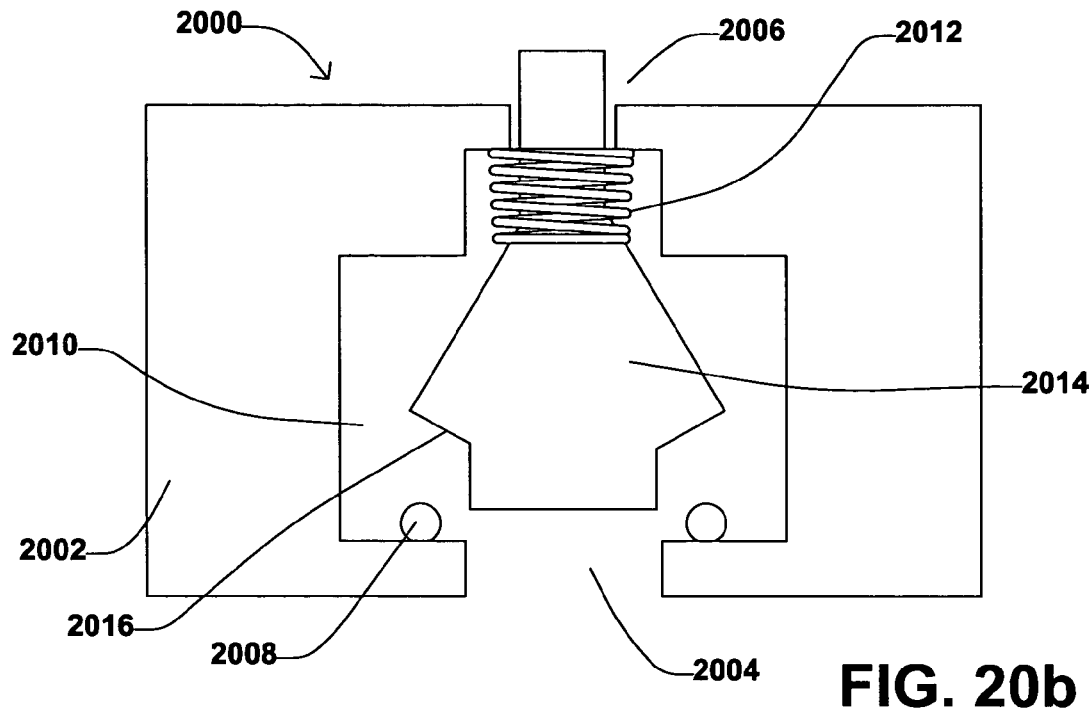

In another exemplary embodiment, FIG. 20a and FIG. 20b include illustrations of an exemplary valve 2000. The valve 2000 can include a valve body 2002 having an inlet opening 2004, a chamber 2010, and an effluent opening 2006. The valve body also can include a valve stem 2014 and a spring 2012. The spring 2012 can surround a portion of and can engage the valve stem 2014 to provide a motivating force away from the effluent opening 2006 and toward the inlet opening 2004.

The valve body 2002 can include a seat 2008 and the valve stem 2014 can include a seal 2016 configured to engage the seat 2008. As illustrated at FIG. 20a, the seal 2016 can engage the seat 2008 to prevent agent flow from a reservoir. In particular, the valve 2000 can be in the closed position illustrated in FIG. 20*a* when the reservoir has a pressure that is insufficient to overcome the force of the spring 2012. When the pressure increases, the valve 2000 can move to an open position illustrated in FIG. 20*b* in which the seal 2016 disengages from the seat 2008. Such a valve 2000 can be used in conjunction with a reservoir storing degradation agent, for example.

While the valves illustrated in FIG. 19*a*, FIG. 19*b*, FIG. 19*c*, FIG. 20*a*, and FIG. 20*b* are described in relation to specific control strategies for agent release, such valves can be used to implement other control strategies. Further, the valves can be configured based on their selection and the selection of components, such as springs. For example, a spring can be selected such that the valve opens or closes in response to a selected pressure or range of pressures selected from ranges between about 0.1 to about 2000 psi, such as between about 0.5 to about 100 psi. In particular, a valve can be selected based at least in part on an osmotic agent or based at least in part on the released agent. In addition, such valves are provided as examples, and other valves not illustrated can be used to implement the described control strategy.

Exemplary Method of Use

Figure 21:
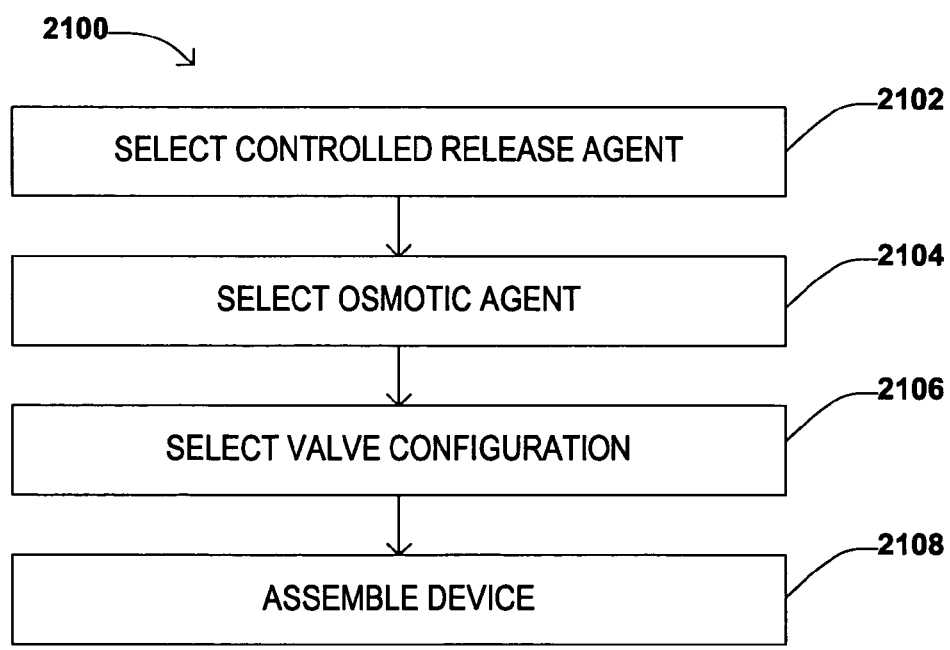
FIG. 21 includes a flow diagram of an exemplary method for preparing a controlled release device.

In an exemplary method, the device can be configured to implement a desired controlled release strategy. FIG. 21 includes an illustration of an exemplary method 2100 to configure a device for a particular patient condition. For example, an agent can be selected for each reservoir of the device, as illustrated at 2102. A device including two reservoirs can include a degradation agent and an osteogenerative agent, for example. In another example, a device including two or more reservoirs can include two or more agents. In a particular example, a device including two or more reservoirs can include an osteogenerative agent, such as an osteoconductive agent, in at least one of the reservoirs, and can include a degradation agent in at least on of the reservoirs.

Based on the agents selected, a controlled release strategy can be implemented by configuration of the reservoir driver and valves. For example, an osmotic agent can be selected, as illustrated at 2104. In a particular example, the osmotic agent and concentrations and variations thereof can be selected to provide a particular response to average pressure or hydration conditions of surrounding tissue. In particular, the osmotic agent can provide a desired pressure response to conditions of the soft tissue, such as the nucleus pulposus or the zygapophyseal joint.

In conjunction with the expected pressure response of the osmotic agent, a valve configuration can be selected, as illustrated at 2106. For example, springs can be selected that provide the prescribed response to the expected pressures effected by the osmotic agent, in situ.

Once a configuration is selected, the device can be configured and assembled, as illustrated at 2008. For example, the device can be configured at the time of manufacture based on an expected application. In another example, the device can be configured by a healthcare provider prior to implantation. In a particular example, the selected agents can be injected into the reservoirs by refill ports, the springs can be added to the valve assemblies, and a cartridge including the osmotic agent can be placed within the device.

Device Implantation

The device or at least a portion of the device can be inserted into the nucleus pulposus of an intervertebral disc of a patient. For example, the device can be implanted as a whole within the nucleus pulposus. Alternatively, the device can be implanted within or in proximity to a zygapophyseal joint.

Figure 22:
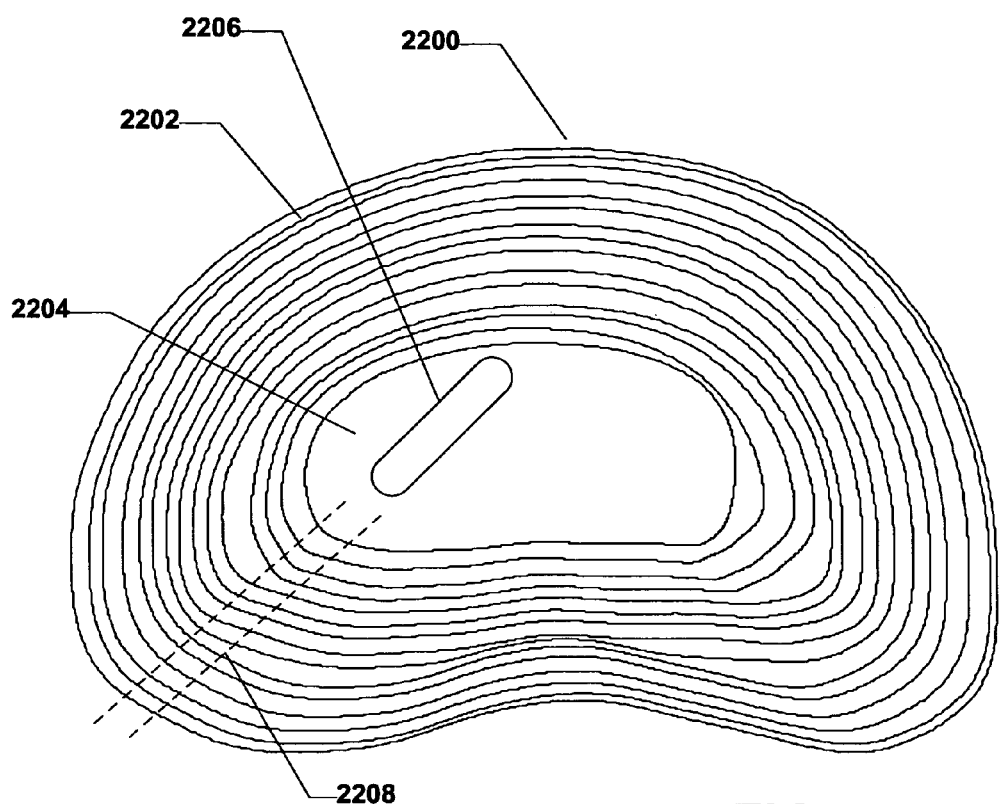
FIG. 22 includes an illustration of an exemplary intervertebral disc.

FIG. 22 includes an illustration of an exemplary intervertebral disc 2200 including an annulus fibrosis 2202 and a nucleus pulposus 2204. A device 2206 can be inserted into the nucleus pulposus 2204 through a passage 2208 through the annulus fibrosis 2202. In an example, the passage 2208 is formed and the device 2206 can be guided through a cannula or an instrument having a lumen therethrough. Once the device 2206 is inserted into the nucleus pulposus 2204, the passage 2208 in the annulus fibrosis 2202 can be sealed using a tissue sealant, scaffold plug, or any combination thereof. In a particular example, the tissue sealant or scaffold plug includes regenerative agents, such as growth factors.

Figure 23:
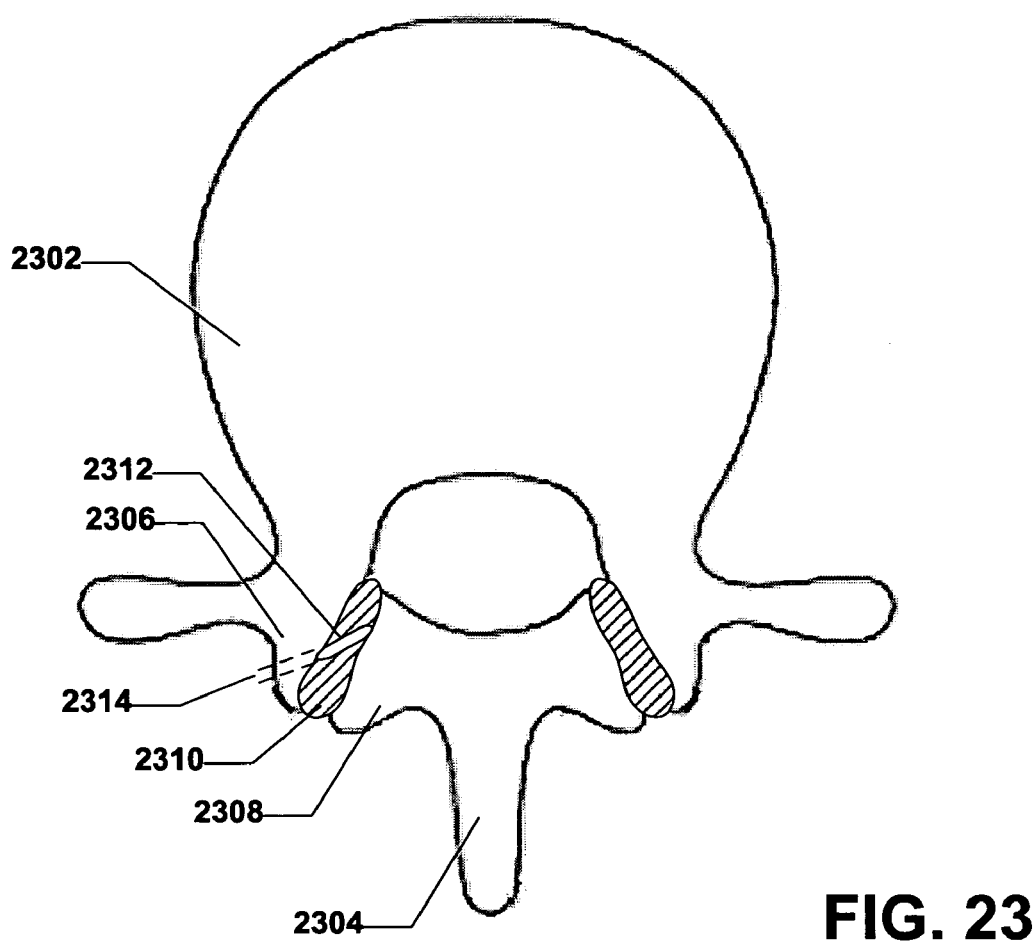
FIG. 23 includes an illustration of an exemplary zygapophyseal joint.

In a further exemplary embodiment illustrated in FIG. 23, an implantable device 2312 is inserted into a zygapophyseal joint 2310 through an articular process, such as a superior articular process 2306 of an inferior vertebra 2302. Alternatively, the implantable device 2312 can be inserted through the inferior articular process 2308 of the superior vertebra 2304. In an exemplary embodiment, the implantable device 2312 is inserted through an access 2314 drilled into an articular process. The device 2312 can engage one or both of the articular processes 2306 or 2308. Alternatively, the device 2312 can be positioned within the zygapophyseal joint to not engage the articular processes 2306 or 2308. While the device 2312 is illustrated without a tail and having a single housing, the device 2312 can be configured with a tail or with an additional housing. The access 2314 can be sealed with a ceramic material, bone cement, tissue sealant, or any combination thereof.

In a particular embodiment, implantable devices can be inserted into the intervertebral disc and the two articular processes associated with two adjacent vertebrae. As such, the implanted devices can influence bone growth to fuse the two adjacent vertebrae together at three locations: between the vertebral bodies, between the left articular processes, and between the right articular processes.

In an exemplary embodiment, a healthcare provider can monitor the device. Based on the data received from the device, the healthcare provider can adjust treatment of the patient, such as changing a setting of the device or injecting an additional agent. For example, once osteogeneration has been initiated, the healthcare provider can inject or implant additional osteogenerative material. For example, the healthcare provider can inject an osteoconductive gel or additional cellular material, such as stem cells. In another example, the healthcare provider can inject an osteoconductive material, such as collagen; a calcium phosphate, such as hydroxyapatite, tricalcium phosphate, or fluorapatite; demineralized bone matrix; calcium sulfate; or any combination thereof. In particular, a surgeon can inject stem cells that respond to the osteogenerative agent being release from the implanted device. In a particular embodiment, the stem cells can be injected into a refill port of the implantable device. In a further embodiment, the healthcare provider can inject additional osteogenerative material in response to radiographic testing. Alternatively, the healthcare provider can inject additional osteogenerative material after a period of time.

Patient Treatment Using an Implantable Device

Typically, the embodiments of the implantable controlled release device described above can be used to treat conditions associated with an intervertebral disc. For example, a patient can have undergone a prior discectomy or can have experienced a herniated disc. In another example, a scan of the patient, such as a computed tomography (CT) scan or a magnetic resonance imaging (MRI) scan, can indicate a problem in a particular intervertebral disc. In such a case, a device can be implanted in the patient.

In general, the device can be configured and filled with an agent or agents prior to implantation. The device can be implanted within the nucleus pulposus of the intervertebral disc and release agents in response to conditions within the intervertebral disc. For example, once implanted, an osmotic driver can hydrate, resulting in a pressure within a reservoir. Based on the pressure within the reservoir, a valve can open or close and release or prevent the release of an agent.

The device can be included in a kit that includes agents to be inserted into the device. The kit can also include one or more osmotic agents and can include one or more valve springs or valves. Alternatively, the device can be provided with the agent within the device. In addition, the device can include a refill port. An agent can be injected into the port to refill a reservoir.

CONCLUSION

With the implanted device described above, osteal structures can be fused or bone growth can be effected. In particular, such devices can be implanted using laparoscopic techniques. Such devices can further reduce the likelihood that a more invasive disc replacement implant will be used. In a particular embodiment, the device can be used to reduce patient discomfort and patient pain or neuro-deficit.

The above-disclosed subject matter is to be considered illustrative, and not restrictive, and the appended claims are intended to cover all such modifications, enhancements, and other embodiments that fall within the true scope of the present invention. For example, it is noted that the components in the exemplary embodiments described herein as having a particular function or as being located in a particular housing are illustrative and it is noted that such components can perform additional functions or be located in different configurations. Thus, to the maximum extent allowed by law, the scope of the present invention is to be determined by the broadest permissible interpretation of the following claims and their equivalents, and shall not be restricted or limited by the foregoing detailed description.

What is claimed is:

1. A device comprising:
   a first reservoir configured to include an osteogenerative agent;
   a second reservoir configured to include a degradation agent;
   a first valve in fluid communication with the first reservoir, wherein the first valve is configured to open in response to a first soft tissue condition of pressure or hydration and close in response to a second soft tissue condition;
   a second valve in fluid communication with the second reservoir, wherein the second valve is configured to remain closed during the first soft tissue condition and the second soft tissue condition and is configured to open in response to a third soft tissue condition; and
   an osmotic driver coupled to the first reservoir and the second reservoir.

2. The device of claim 1, wherein the second valve is configured to open upon implantation.

3. The device of claim 1, wherein the first soft tissue condition is a low pressure or hydration condition.

4. The device of claim 1, wherein the second soft tissue condition is a pressure or hydration condition higher that the first soft tissue condition.

5. The device of claim 1, wherein the third soft tissue condition is a pressure or hydration condition higher than the first soft tissue condition and the second soft tissue condition.

6. The device of claim 1, wherein the osteogenerative agent includes an osteoconductive agent.

7. The device of claim 1, wherein the osteogenerative agent includes an osteoinductive agent.

8. The device of claim 7, wherein the osteoinductive agent includes bone morphogenetic protein, demineralized bone matrix, transforming growth factor (TGF), osteoblast cells, growth and differentiation factor (GDF), LIM mineralized protein (LMP), platelet derived growth factor (PDGF), insulin-like growth factor (ILGF), or any combination thereof.

9. The device of claim 1, wherein the degradation agent includes chymopapain, collagenase, chondroitinase, keratanase, human proteolytic enzymes, papaya proteinase, or any combination thereof.

* * * * *

UNITED STATES PATENT AND TRADEMARK OFFICE
CERTIFICATE OF CORRECTION

| | | |
|---|---|---|
| PATENT NO. | : 7,879,027 B2 | |
| APPLICATION NO. | : 11/517771 | |
| DATED | : February 1, 2011 | |
| INVENTOR(S) | : Trieu | |

It is certified that error appears in the above-identified patent and that said Letters Patent is hereby corrected as shown below:

On the Title Pg, Item (73), under "Assignee", Line 1, delete "Inc." and insert -- Inc., Warsaw, IN (US) --, therefor.

On Page 2, Item (56), under "OTHER DOCUMENTS", Line 10, delete "391481" and insert -- 391488; --, therefor.

In Column 2, Line 50, delete "joint; and" and insert -- joint; --, therefor.

In Column 2, Line 52, delete "components." and insert -- components; and --, therefor.

In Column 12, Lines 11-12, delete "polyuerethane or compolyers" and insert -- polyurethane or copolymers --, therefor.

In Column 17, Line 62, delete "polyuerethane or compolyers" and insert -- polyurethane or copolymers --, therefor.

Signed and Sealed this
Fifth Day of April, 2011

David J. Kappos
*Director of the United States Patent and Trademark Office*